United States Patent
Boudeffa et al.

(10) Patent No.: US 10,465,169 B2
(45) Date of Patent: Nov. 5, 2019

(54) METHOD FOR PURIFYING ENVELOPED VIRUSES OR VIRAL VECTORS

(71) Applicant: GENETHON, Evry (FR)

(72) Inventors: Driss Boudeffa, Montreal (CA); Otto-Wilhelm Merten, Crespieres (FR); David Fenard, Mennecy (FR)

(73) Assignee: GENETHON, Evry (FR)

(*) Notice: Subject to any disclaimer, the term of this patent is extended or adjusted under 35 U.S.C. 154(b) by 0 days.

(21) Appl. No.: 15/105,880

(22) PCT Filed: Dec. 17, 2014

(86) PCT No.: PCT/FR2014/053406
§ 371 (c)(1),
(2) Date: Sep. 15, 2016

(87) PCT Pub. No.: WO2015/092287
PCT Pub. Date: Jun. 25, 2015

(65) Prior Publication Data
US 2017/0002332 A1    Jan. 5, 2017

(30) Foreign Application Priority Data
Dec. 17, 2013    (FR) ..................... 13 62835

(51) Int. Cl.
| | | |
|---|---|---|
| C07K 16/24 | (2006.01) | |
| A61K 39/395 | (2006.01) | |
| C07K 16/00 | (2006.01) | |
| C12N 15/113 | (2010.01) | |
| A61K 39/00 | (2006.01) | |
| C12N 7/00 | (2006.01) | |
| C12N 15/86 | (2006.01) | |

(52) U.S. Cl.
CPC ............. *C12N 7/00* (2013.01); *C12N 15/86* (2013.01); *C12N 2740/15043* (2013.01); *C12N 2740/15051* (2013.01); *C12N 2740/16043* (2013.01); *C12N 2740/16051* (2013.01)

(58) Field of Classification Search
CPC ........ C12N 2310/321; C12N 2310/322; C07K 16/241; A61K 39/3955; A61K 2039/505
See application file for complete search history.

(56) References Cited

U.S. PATENT DOCUMENTS

| 2014/0315294 A1 | 10/2014 | Marceau et al. |
| 2016/0230147 A1 | 8/2016 | Fenard |

FOREIGN PATENT DOCUMENTS

| WO | WO 2006/052813 | 5/2006 |
| WO | WO2006052813 | * 5/2006 |
| WO | WO 2007/123961 | 11/2007 |
| WO | WO2007123961 | * 11/2007 |
| WO | WO 2009/153563 | 12/2009 |
| WO | WO2009153563 | * 12/2009 |
| WO | WO 2013/001041 | 1/2013 |
| WO | WO 2013/076309 | 5/2013 |
| WO | WO 2015/036713 | 3/2015 |

OTHER PUBLICATIONS

Anonymous: "Purification of influenza A/H1N1 using Capto(TM) Core 700", GE Healthcare Life Sciences: pp. 1-8.*
Rodrigues et al. "Purification of retroviral vectors for clinical application: Biological implications and technological challenges", Journal of Biotechnology, 2006, 127(3):520-541.*
Rodrigues et al., "Screening anion-exchange chromatographic matrices for isolation of onco-retroviral vectors", Journal of Chromatography B, 2006, 837:59-68.*
De Las Mercedes Segura, M. et al. "Downstream processing of oncoretroviral and lentiviral gene therapy vectors" *Biotechnology Advances*, May 2006, pp. 321-337, vol. 24, No. 3.
Herzer, S. et al. "Isoelectric titration curves of viral particles as an evaluation tool for ion exchange chromatography" *Life Science News*, 2003, pp. 16-18, vol. 13.
McTaggart, S. et al. "Effects of Culture Parameters on the Production of Retroviral Vectors by a Human Packaging Cell Line" *Biotechnology Progress*, Sep. 2000, pp. 859-865, vol. 16, No. 5.
Morizono, K. et al. "Transient low pH treatment enhances infection of lentiviral vector pseudotypes with a targeting Sindbis envelope" *Virology*, Nov. 10, 2006, pp. 71-81, vol. 335, No. 1.
Rodrigues, T. et al. "Purification of retroviral vectors for clinical application: Biological implications and technological challenges" *Journal of Biotechnology*, Dec. 2006, pp. 520-541, vol. 127, No. 3.
Anonymous "Purification of influenza A/H1N1 using Capto™ Core 700" *GE Healthcare Life Sciences*, Mar. 2012, pp. 1-8, retrieved from the internet, URL:http://wolfson.huji.ac.il/purification/PDF/HCIC/GE_CaptoCore700PurificInfluenzaAH1N1.pdf, XP055141530.
Written Opinion in International Application No. PCT/FR2014/053406, dated Mar. 17, 2015, pp. 1-8.
Higashikawa, F., et al., "Kinetic Analyses of Stability of Simple and Complex Retroviral Vectors," *Virology*, Feb. 2001, vol. 280, No. 1, pp. 124-131.
Holic, N., et al., "Influence of Mildly Acidic pH Conditions on the Production of Lentiviral and Retroviral Vectors," *Human Gene Therapy Clinical Development*, Sep. 1, 2014, vol. 25, No. 3, pp. 178-185.
"Protocol: Lenti-Viral Transfection/Transduction," Nov. 2, 2010, XP055127370, pp. 1-2, retrieved from the Internet on Jul. 7, 2014: http://research.jax.org/faculty/mills/protocols/lentiviral_transfection.pdf.
Written Opinion in International Application No. PCT/FR2014/052279, dated Dec. 22, 2014, pp. 1-7.
Williams, A.C., et al., "An acidic environment leads to p53 dependent induction of apoptosis in human adenoma and carcinoma cell lines: implications for clonal selection during colorectal carcinogenesis," *Oncogene*, 1998, vol. 18, pp. 3199-3204.

* cited by examiner

*Primary Examiner* — Barry A Chestnut
(74) *Attorney, Agent, or Firm* — Saliwanchik, Lloyd & Eisenschenk

(57) ABSTRACT

The invention relates to a process for purifying enveloped viruses. The process of the invention is useful for recovering at a large scale enveloped viruses under conditions complying with good manufacturing practices and allowing viruses of a clinical grade to be obtained.

23 Claims, 6 Drawing Sheets

METHOD FOR PURIFYING ENVELOPED VIRUSES OR VIRAL VECTORS

CROSS-REFERENCE TO RELATED APPLICATION

Figure 1:
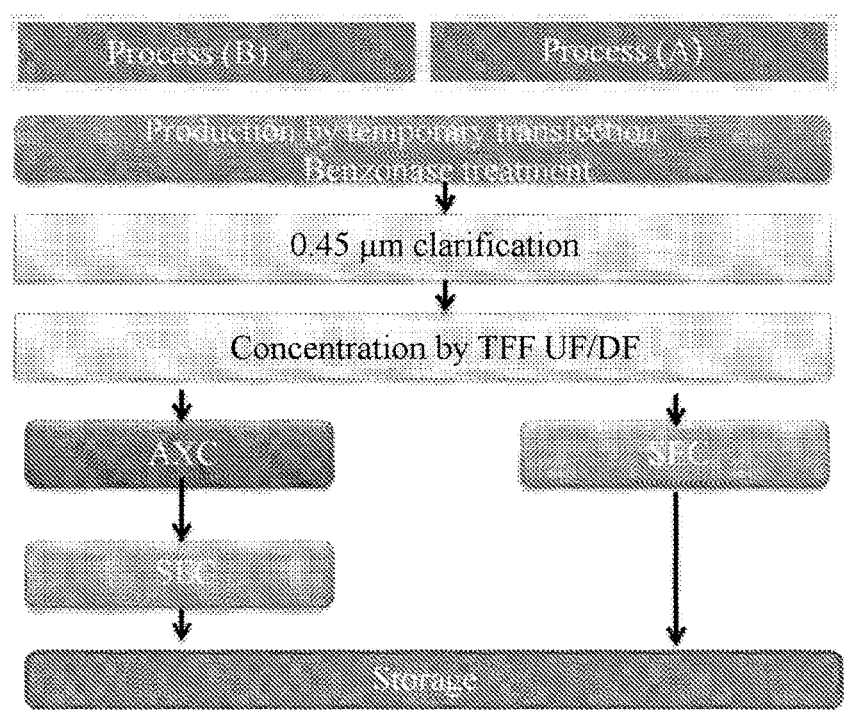

This application is the U.S. national stage application of International Patent Application No. PCT/FR2014/053406, filed Dec. 17, 2014.

The invention relates to a process for purifying enveloped viruses. The process of the invention is useful for large scale recovery of enveloped viruses under conditions complying with good manufacturing practices and allowing obtaining clinical-grade viruses.

TECHNOLOGICAL BACKGROUND

Lentiviral vectors derived from the human immunodeficiency virus (notably HIV-1) are part of the vectors the most used for gene therapy. These vectors are generally pseudotyped with glycoproteins from other viruses: gibbon ape leukemia virus (GALV; GaLV-TR glycoproteins), vesicular stomatitis virus (VSV-g), or measles virus (MV). Processes for purifying clinical batches of lentiviral vectors pseudotyped with the VSV-G protein have been described (Schweizer and Merten, 2010). However, viral vectors pseudotyped with other envelope proteins, and more particularly with glycoproteins derived from GaLV or MV, are not widely used since no satisfactory purifying protocol is available at the present time. The major limiting obstacle for the purification of this type of pseudotyped vectors is related to the instability and fragility of certain membrane glycoproteins. However, these vectors are of particular interest as regards their less broad tropism than that of vectors pseudotyped with the VSV-G protein. For example, the vectors pseudotyped with a glycoprotein derived from GALV have more restricted tropism and more particularly target hematopoietic stem cells. Making available an efficient process for purifying vectors pseudotyped with GALV glycoproteins therefore represents a major challenge in the field of gene therapy.

The inventors therefore proposed the development of a process for purifying enveloped viruses, and notably viruses pseudotyped with the envelope glycoprotein GaLV or by other envelope proteins, aiming at producing preparations of viruses for clinical use.

SUMMARY OF THE INVENTION

The present invention results from the unexpected observation made by the inventors of the influence of the pH of the solutions used during purification of an enveloped virus, and of the positive influence of certain additives on the yield of said purification.

The present invention in particular results from the observation of the striking improvement in the purification of enveloped viruses when acid buffers are used during anion exchange chromatography. The object of the invention is therefore a process for purifying enveloped viruses comprising an anion exchange chromatography, the buffers used during said chromatography being of a pH of less than 6.

In particular, the pH may notably be comprised between 5.5 and 6. According to an alternative, the pH of the buffers used during anion exchange chromatography is greater than or equal to 6 and further comprises a polyol.

The inventors were able to show that by adding a polyol in one or several of the buffers used during one or several steps of a process for purifying an enveloped virus, it was possible to obtain a substantial increase in the purification yield. In particular, the improvement of the yield of a purification comprising an ultrafiltration/diafiltration step followed by anion exchange chromatography is observed when the buffers used during this chromatography comprise a polyol.

The inventors also propose inversion of the order of the anion exchange chromatography steps and of ultrafiltration/diafiltration steps, notably a tangential flow filtration (TFF), used during the purification. The application of an ultrafiltration/diafiltration, notably a TFF, before an anion exchange chromatography allows a substantial improvement in the yield of the purification of an enveloped vector. The invention therefore also relates to a process for purifying an enveloped virus, comprising, in this order, an ultrafiltration/diafiltration step, notably a TFF step, followed by an anion exchange chromatography step.

Moreover the invention relates to a process for purifying enveloped viruses, said process comprising an ultrafiltration/diafiltration step, notably a TFF step, said step being carried out by using buffers containing a polyol.

The invention is more particularly adapted to the purification of viruses pseudotyped with a glycoprotein derived from GaLV. Until the availability of the present invention, the viruses pseudotyped with this type of glycoproteins were considered "non-purifiable". The different studies carried out on these viral vectors applied raw preparations of non-purified vectors because of the fragility of the GaLV pseudotyped vectors. Unexpectedly, the inventors were able to show a substantial improvement in the purification yield by means of the process of the invention. They were also able to show that this process allows improvement in the yield of the purification of viruses pseudotyped with other envelope glycoproteins, notably with VSV-G and MV glycoproteins.

DETAILED DESCRIPTION OF THE INVENTION

Production of Enveloped Viruses and Vectors

The production of enveloped viruses or vectors is well known in the state of the art. One skilled in the art may refer to general knowledge in this field, notably represented by Ansorge et al. 2010; Schweizer and Merten 2010; Rodrigues et al. 2011.

The produced virus is notably an enveloped viral vector. The viral vector is notably derived from a retrovirus, in particular a lentivirus. The produced retroviral vectors are notably derived from alpha retroviruses (such as ALV for avian leukosis virus), from beta retroviruses (such as MMTV for mouse mammary tumor virus), from gamma retroviruses (such as the different types of MLV for murine leukemia virus), from delta retroviruses (such as the different types of HTLV for human T-lymphotropic virus), from epsilon retroviruses (such as WDSV for Walleye dermal sarcoma virus), from spumavirus (such as HFV for human foamy virus and SFV for simian foamy virus), from primate lentiviruses such as the different types of human immunodeficiency viruses (HIV for human immunodeficiency virus), the different types of simian immunodeficiency viruses (SIV for simian immunodeficiency virus), or from non-primate mammal lentiviruses such as the equine infectious anemia virus (EIAV for equine infectious anemia virus), from the feline immunodeficiency virus (FIV for feline immunodeficiency virus), the caprine arthritis-encephalitis virus (CAEV for caprine arthritis-encephalitis virus), or the ovine visna-maedi virus (VMV for visna maedi virus).

According to a particular embodiment, the enveloped virus, notably the retroviral vector, in particular lentiviral vector, is pseudotyped, i.e. it comprises an envelope glycoprotein derived from a virus different from the virus from which is derived the retroviral particle, a modified envelope glycoprotein or a chimeric envelope glycoprotein. According to a particular embodiment, the retroviral vector is pseudotyped with an envelope glycoprotein derived from the vesicular stomatitis virus (VSV-G), from the measles virus (MV for measles virus), or modified MV virus (notably modified with an anti-CMHII antibody), from the Baboon Endogenous Virus (BaEV) or from the gibbon ape leukemia virus (GALV), although one skilled in the art may contemplate the use of other viral envelope glycoproteins (Frecha et al. 2008). According to a particular embodiment, the enveloped virus, notably the retroviral vector, more particularly lentiviral vector, is pseudotyped with a modified envelope glycoprotein such as GALVTR (GALV envelope glycoprotein, in which the intravirion C-terminal end has been replaced with the C-terminal end of the envelope glycoprotein of the amphotropic human leukemia virus (A-MLV), thus allowing very efficient incorporation of the envelope glycoprotein into the lentiviral particle) (Christodoulopoulos and Cannon 2001). According to a particular embodiment, the enveloped virus, notably the retroviral vector, more particularly lentiviral vector, is pseudotyped with a chimeric envelope glycoprotein such as the envelope glycoprotein of the measles virus into which has been inserted a fusion protein coding the variable region of heavy and light chains of an immunoglobulin (scFv for single chain variable fragment) or a protein with repeated ankyrin domains (DARPins for designed ankyrin repeat proteins) for allowing specific targeting of a given receptor at the surface of the target cells (Anliker et al. 2010; Münch et al. 2011). According to a particular embodiment, the lentiviral vector is pseudotyped with an envelope derived from the GALV virus, from the vesicular stomatitis virus (e.g. a VSV-G envelope protein), or from the measles virus, although one skilled in the art may contemplate the use of other envelope proteins.

The enveloped virus may moreover contain a transgene of interest introduced into its genome. Of course, the transgene of interest will depend on the specific use for which the enveloped viral vector is intended. Illustratively, let us mention a transgene of interest coding for a therapeutic RNA (e.g., a transgene of interest coding for an antisense complementary RNA of a target RNA or DNA sequence), a transgene of gene therapy coding for a protein deficient or absent in a subject affected with a pathology, or a transgene used for vaccination with DNA, i.e. a transgene coding for a protein, the expression of which will induce vaccination of the recipient body against said protein. According to a particular embodiment, an enveloped viral vector which may be used in gene therapy is produced, and then purified. The production process used is advantageously compatible with good laboratory practices and gives the possibility of contemplating a large scale production of enveloped viral vectors, notably retroviral vectors, notably lentiviral vectors, in particular pseudotyped lentiviral vectors (in particular with GALV envelope proteins for a retrovirus or GALVTR for a lentivirus, VSV-G, or MV).

According to a preferred embodiment for producing a lentiviral vector, the four following elements are introduced into the host cell: an expression cassette comprising a lentiviral gene gagpol, an expression cassette comprising a lentiviral gene rev, an expression cassette of a transgene of interest, comprised between a lentiviral LTR-5' and a lentiviral LTR-3', and an expression cassette of envelope glycoprotein(s).

In a particular embodiment, the enveloped virus, notably a retroviral vector, more particularly a lentiviral vector, is produced from a stable line expressing one or several elements required for producing an enveloped virus (Miller 2001; Rodrigues et al. 2011), such as the human production line GPRG-EF1α-hγ$_c$OPT which constitutively produces a lentiviral vector derived from HIV-1 pseudotyped with the envelope glycoprotein VSV-G (Greene et al. 2012), or for example the murine production line PG13-MFG-GFP which constitutively produces the MLV gammaretroviral vector pseudotyped with the envelope glycoprotein GaLV (Miller et al. 1991). In a particular embodiment, the enveloped virus is produced from a mammal host cell transfected transiently with one or several plasmids coding for the elements required for producing the virus. According to an alternative allowing production of a lentiviral vector, said elements are introduced into the cell by means of 4 plasmids: one plasmid bearing an expression cassette comprising a lentiviral gagpol gene, one plasmid bearing an expression cassette comprising a lentiviral rev gene, one transfer plasmid comprising an expression cassette of a transgene of interest, comprised between a lentiviral LTR-5' and LTR-3' and one plasmid bearing an expression cassette of envelope glycoprotein(s).

The host cell may be selected from any cell allowing production of an enveloped virus. According to a particular embodiment, said cell is selected from a human cell (HEK293, HEK293T, HEK293FT, Te671, HT1080, CEM), a muridae cell (NIH-3T3), a mustelidae cell (Mpf), and a canid cell (D17) (Miller and Chen 1996; Miller 2001; Merten 2004; Rodrigues et al. 2011; Stacey and Merten 2011).

The cells are cultivated in a medium suitable for cultivation of mammal cells and for producing an enveloped virus. The medium may moreover be supplemented with additives well known in the field such as antibiotics and serum (notably fetal calf serum, etc.) added in suitable concentrations. The medium used may notably comprise serum or be serum-free. The culture media for mammal cells are well known in the field. As such mention may be made of DMEM (Dulbecco's Modified Eagle's Medium), RPMI1640 or a mixture of various culture media, including for example DMEM/F12, or a serum-free medium like optiMEM®, optiPRO®, optiPRO-SFM®, CD293®, Freestyle F17® (Life Technologies) or Ex-Cell® 293 (Sigma-Aldrich).

In the processes using transiently transfected cells, any agent allowing transfection of plasmids may be used. Use may notably be made of calcium phosphate or polyethylenimine, although other agents may be contemplated by one skilled in the art (Ansorge et al. 2010). The conditions (notably amount of plasmid(s), ratio between the plasmids, ratio between the plasmid(s) and the transfection agent, the type of medium, etc.) and the transfection time may be adapted by one skilled in the art according to the characteristics of the produced virus and/or of the transgene introduced into the transfer plasmid.

The enveloped virus is then harvested from the supernatant of the culture according to methods well known in the field.

According to a particular embodiment, the culture medium used has a neutral pH (e.g. comprised between 7 and 7.4, notably 7, 7.1, 7.2, 7.3 or 7.4) conventionally used in the state of the art for cultivating cells and producing viruses. According to a particular embodiment, the production process used comprises the cultivation of producing cells in a moderately acid medium. While the state of the art exhibits neutrality of the culture media as a necessary condition for optimum cultivation of cells and optimum production of enveloped viruses and vectors, it was discovered that moderately acid conditions gave the possibility on the contrary of significantly improving the production of an enveloped virus, notably of a lentivirus, in particular a pseudotyped lentivirus (for example with the protein GaLV (or GaLVTR), VSV-G, or measles virus envelope proteins).

According to an alternative, the production of enveloped vectors is achieved under a moderately acid condition. The expression "moderately acid condition" designates the pH of an aqueous solution comprised between 5 and 6.8, in particular between 5.5 and 6.5, more particularly between 5.8 and 6.2. According to a particular embodiment, the pH of the culture medium is of about 6. The selected pH will also depend on the buffering power of the culture medium used, which one skilled in the art may easily determine taking into account his/her general knowledge. One skilled in the art is able to modify the pH of a solution, notably the pH of a cell culture medium. He/she may notably introduce into said solution a solution of an acid, notably of a strong acid such as hydrochloric acid. If need be, a solution of a base, notably a strong base such as sodium hydroxide, may be used for readjusting the pH by raising it in order to attain the desired value.

According to a particular embodiment, the production of the enveloped virus comprises the following steps:
- transient transfection of HEK293T cells by means of one or several plasmids coding for the elements required for production of said enveloped vector or for the use of stable producing cells producing constitutively the vectors or after induction;
- the culture of said cells in a suitable medium, for which the pH is of about 6 or of about 7; and
- harvesting the enveloped virus in the supernatant of the culture.

According to an alternative of this embodiment, the produced enveloped virus is a lentivirus produced after transfection of the cells by means of four plasmids: one plasmid bearing an expression cassette comprising a lentiviral gagpol gene, one plasmid bearing an expression cassette comprising a lentiviral rev gene, one transfer plasmid comprising an expression cassette of a transgene of interest, comprised between a lentiviral LTR-5' and LTR-3' and one plasmid bearing an expression cassette of envelope glycoprotein(s). According to an alternative, the envelope protein is derived from the GaLV virus (in particular the modified glycoprotein GaLVTR for lentiviral vectors), from the VSV virus (in particular the VSV-G envelope) or from the measles virus (MV).

Purification of Enveloped Viruses and Vectors

As we will see in the examples of this application, the purification yield of enveloped viruses produced may be strikingly improved by adapting the pH conditions of the buffers used during said purification.

In particular, the enveloped viruses may be very advantageously purified according to a novel process comprising the use of acid buffers during anion exchange chromatography. Thus, the invention in particular relates to a process for purifying an enveloped virus, the process comprising an anion exchange chromatography step, the buffer(s) used during this anion exchange chromatography step being of a pH of less than or equal to 6.9. The enveloped virus may notably be purified from the culture medium of a cell culture of cells producing said enveloped virus. In a particular embodiment, the pH of the buffer(s) used during the anion exchange chromatography step is comprised between 4.5 and 6.2 (notably equal to 4.5, 4.6, 4.7, 4.8, 4.9, 5.0, 5.1, 5.2, 5.3, 5.4, 5.5, 5.6, 5.7, 5.8, 5.9, 6.0, 6.1 or 6.2), more particularly between 5 and 6 (notably equal to 5.0, 5.1, 5.2, 5.3, 5.4, 5.5, 5.6, 5.7, 5.8, 5.9 or 6.0). According to a particular embodiment, the pH is comprised between 5 and 6, or between 5 and 5.9, the pH being more particularly equal to 5.0, 5.1, 5.2, 5.3, 5.4, 5.5, 5.6, 5.7, 5.8 or 5.9. In particular, the pH is comprised between 5.5 and 6 (for example equal to 5.5, 5.6, 5.7, 5.8, 5.9 or 6.0), the pH being more particularly of about 5.5 (e.g. 5.4, 5.5 or 5.6) or 6 (e.g. 5.9, 6 or 6.1), still more particularly 5.5. The anion exchange chromatography may be preceded with or followed by, preferably preceded with, an ultrafiltration step, in particular with ultrafiltration/diafiltration, notably with a tangential flow filtration. According to an embodiment, the anion exchange chromatography precedes the ultrafiltration. According to an alternative embodiment, the ultrafiltration precedes the anion exchange chromatography, the latter embodiment being preferred.

The inventors have also shown the advantage of using a polyol, notably sucrose, in buffers used during anion exchange chromatography, when said buffers have a pH greater than or equal to 6, notably a pH comprised between 6 and 8 (notably a pH equal to 6.0, 6.1 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0). The invention therefore also relates to a process for purifying an enveloped virus comprising an ultrafiltration/diafiltration step followed by anion exchange chromatography step, said chromatography being carried out by using buffers with a pH greater than or equal to 6, notably a pH comprised between 6 and 8, more particularly between 7 and 8 (notably a pH equal to 7.0, 7.1, 7.2, 7.3, 7.4, 7.5, 7.6, 7.7, 7.8, 7.9 or 8.0), containing a polyol.

The buffer(s) used during the ultrafiltration/diafiltration step, more particularly TFF, may also be acid, neutral or basic buffers.

One skilled in the art is capable of modifying the pH of a solution, notably the pH of a buffer used during a step for purifying enveloped viruses. He/she may notably introduce into said solution a solution of an acid, notably of a strong acid such as hydrochloric acid, for reducing the pH or adjusting it. If need be, a solution of a base, notably of a strong base such as sodium hydroxide, may be used for obtaining a basic pH or for readjusting the pH by raising it in order to attain a desired acid value. Of course, one skilled in the art will ensure the use of an adequate formulation for obtaining a solution with a suitable buffer power at the desired pH.

The solution loaded on or in the ultrafiltration/diafiltration device or on the anion exchange chromatography column may correspond to the cell culture supernatant optionally pre-treated with a benzonase and/or with low speed centrifugation and/or a clarification. It is understood that this optionally pre-treated culture supernatant does not correspond to a "purification buffer". However, its pH may also be adjusted before loading it if need be. If the production was carried out at a neutral or acid pH, the optionally pre-treated culture supernatant may be directly loaded, or its pH may be reduced or increased before loading it. It is also possible to contemplate the addition of additives into the optionally pre-treated culture supernatants before loading it. For example, it is possible to add as soon as this step, a polyol, an antioxidant (notably L-histidine, L-methionine, L-cysteine, glutathione or vitamin C), a metal salt, notably a magnesium salt such as $MgCl_2$ or $MgSO_4$, or any other adequate additive.

According to a particular embodiment, the culture supernatant, optionally pretreated, is directly loaded on or in the ultrafiltration/diafiltration device or on the chromatography column, without pH adjustment and without adding an additive. Acid, basic or neutral pH buffers may be, and preferably are, used beforehand for equilibration of the ultrafiltration/diafiltration device and/or for achieving ultrafiltration/diafiltration or anion exchange chromatography as such.

According to an alternative, the ultrafiltration/diafiltration step is a TFF step. In this alternative, diafiltration is achieved with a buffer, for which the pH is adjusted according to the conditions discussed above. Thus, the buffer used may be an acid buffer, notably a buffer with a pH of less than 6 or a buffer with a pH comprised between 4.5 and 6.2 (notably equal to 4.5, 4.6, 4.7, 4.8, 4.9, 5.0, 5.1, 5.2, 5.3, 5.4, 5.5, 5.6, 5.7, 5.8, 5.9, 6.0, 6.1 or 6.2), notably between 5 and 6 (notably equal to 5.0, 5.1, 5.2, 5.3, 5.4, 5.5, 5.6, 5.7, 5.8, 5.9 or 6.0), in particular a buffer with a pH from 5.5 to 6 (notably equal to 5.5, 5.6, 5.7, 5.8, 5.9 or 6.0), more particularly a buffer with a pH of 5.5. In an alternative, the buffer used is a buffer with a pH greater than or equal to 6, in particular comprised between 6 and 8 (notably a pH equal to 6.0, 6.1 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0), more particularly between 7 and 8 (notably a pH equal to 7.0, 7.1, 7.2, 7.3, 7.4, 7.5, 7.6, 7.7, 7.8, 7.9 or 8.0), comprising a polyol.

The buffers used during the ultrafiltration step and during the diafiltration step may be different or identical. In a particular embodiment, the ultrafiltration step is achieved by means of a buffer having a pH of about 7 (notably a pH comprised between 6.8 and 7.2 (for example equal to 6.8, 6.9, 7.0, 7.1 or 7.2), more particularly a buffer with a pH of 7) and diafiltration is achieved by means of a buffer having a pH comprised between 4.5 and 6.2 (notably equal to 4.5, 4.6, 4.7, 4.8, 4.9, 5.0, 5.1, 5.2, 5.3, 5.4, 5.5, 5.6, 5.7, 5.8, 5.9, 6.0, 6.1 or 6.2), notably a pH comprised between 5 and 6 (notably equal to 5.0, 5.1, 5.2, 5.3, 5.4, 5.5, 5.6, 5.7, 5.8, 5.9 or 6.0), more particularly a buffer with a pH comprised between 5.5 and 6 (notably equal to 5.5, 5.6, 5.7, 5.8, 5.9 or 6.0), in particular a buffer with a pH equal to 5.5.

In an embodiment, the purification process comprises an anion exchange chromatography step followed by an ultrafiltration/diafiltration step. In another embodiment, the purification process comprises an ultrafiltration step followed by an anion exchange chromatography step.

In a particular embodiment, the purification process comprises:
(a) clarification of the cell culture medium;
(b) an ultrafiltration/diafiltration step;
(c) an anion exchange chromatography; and
(d) an exclusion chromatography;
wherein steps (b) and (c) may be inverted. In a preferred embodiment, step (c) follows step (b).

FIG. 1 of this application summarizes the steps of a preferred embodiment of the purification process according to the invention.

According to a particular embodiment, a first clarification step is carried out by filtration of the culture supernatant on a filter, for which the retention threshold is comprised between 0.2 and 0.8 µm, in particular a 0.45 µm filter, and by recovering the enveloped viruses in the filtrate. According to an embodiment, the clarification is achieved by means of a cascade of filters with different retention thresholds, for example with a succession of 0.8, 0.45 and 0.2 µm or else 0.65 and 0.2 µm filters. This clarification step may be preceded with a step of centrifugation of the culture supernatant at a low rate. The centrifugation rate at this step may notably be comprised between 500×g and 1,000×g.

According to a particular embodiment, the ultrafiltration/diafiltration step is notably achieved by filtration with a tangential flow. According to this embodiment, filtration with a tangential flow may be carried out by means of a membrane with hollow fibers or a planar membrane or spiral wound membrane cassette, for which the exclusion size of the pores is comprised between 300 and 800 kDa, in particular between 500 and 750 kDa. According to another embodiment, the exclusion size of the pores is of at least 300, 400, 500, 600, or 700 kDa, or is of 800 kDa. According to a preferred embodiment, the membrane used for filtration with a tangential flow is characterized by an exclusion size of the pores of 750 kDa. According to a particular embodiment, at the end of the ultrafiltration/diafiltration step, the enveloped viruses, notably the enveloped viruses present in the filtrate of the clarification step, are concentrated up to the minimum possible volume, for example at least 5×, at least 10×, 15×, 20×, 25×, 30×, 35×, 40×, 45×, 50×, 55× or 60×. For example, the enveloped viruses are concentrated 36.6× or 50× at the end of the ultrafiltration/diafiltration step. According to another embodiment, the ultrafiltration/diafiltration step allows a reduction in the load of contaminants by more than 70%, 80%, 85%, 90% or more than 95%. According to a particular embodiment, the ultrafiltration/diafiltration step is carried out in the following way: a first concentration is achieved, for example a concentration of 25× (notably, by passing from a volume of 500 mL to a volume of 20 mL), followed by diafiltration with at least 2, 3, 4, 5, 6, 7, 8, 9, or even at least 10 volumes of an acid buffer either containing or not a polyol and/or one or several antioxidants, for example with 10 volumes of buffer; this step is then followed by a second concentration step, notably down to the minimum possible volume, for attaining a concentration of 50× for example.

The anion exchange chromatography substrates are well known in this field. The invention more particularly applies an anion exchange chromatography on a column or on a membrane, more particularly on a column. A preferred embodiment comprises the application of low anion exchange chromatography (notably, DEAE (D)—diethylaminoethyl, PI—polyethylenimine). As such, mention may be made of the use of a substrate selected from a DEAE column. As an illustration, mention may be made of the substrates Monolithe CIM D (BIA Separations), Poros D50 (Life Technologies), Sartobind D (Sartorius), Toyopearl 650C DEAE (Tosoh), etc. In a preferred embodiment, the anion exchange chromatography substrate is an incompressible substrate such as the substrates Monolithe CIM D and Poros D50, giving the possibility of obtaining a better yield than compressible substrates. When the pH of the buffers used during anion exchange chromatography is less than 6, said buffers contain or do not contain a polyol. In particular, it was observed that by the use of buffers with a pH of 5.5 during this step, it was possible to obtain a yield of about 100% of GALVTR pseudotyped lentiviral vectors without requiring the addition of a polyol. This excellent yield level has never been attained to this day and gives the possibility of contemplating the large scale use of this type of vectors, which are particularly advantageous for the reasons discussed earlier. The addition of a polyol has not shown any positive or negative impact on this yield, but their addition may however be contemplated with a purpose of stabilization of the eluted vectors. When the pH of the buffers used is greater than or equal to 6, notably comprised between 6 and 8, the addition of a polyol significantly improves the yield of the purification. Thus, according to the invention, when the pH of the anion exchange chromatography buffers is comprised between about 6 and about 8, said pH's contain a polyol.

In an embodiment, the purified and filtered solution from the ultrafiltration step, more particularly from ultrafiltration/diafiltration is deposited on the chromatography substrate which first of all has been equilibrated by means of an equilibration buffer with a pH of less than 6 optionally containing a polyol. The equilibration buffer and the loading buffer may notably contain an NaCl concentration comprised between 0 and 250 mM. These buffers may notably be compounds which correspond to a Bis-Tris 20 mM buffer, with a pH of 5 to 6 (for example 5.0, 5.1, 5.2, 5.3, 5.4, 5.5, 5.6, 5.7, 5.8, 5.9 or 6.0, notably a pH of 5.5), 5% sucrose, and 2 mM $MgCl_2$ or an equilibration buffer with a pH greater than or equal to 6, notably comprised between 6 and 8 (with a pH equal to 6.0, 6.1 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0), containing a polyol, for example a PBS buffer, with a pH of 7, 5% sucrose or Bis-Tris-propane of pH 8, 5% sucrose, and 2 mM $MgCl_2$. The buffer is introduced at an adequate rate (for example 1 column volume/min or 4 cm/min). The column is then washed with the equilibration buffer, and finally eluted. According to a particular embodiment, the elution of the anion exchange chromatography column is carried out in two steps with a buffer either comprising or not a polyol, notably with a buffer of 0.3 M NaCl, 20 mM Bis-Tris (pH 5 to 6, notably equal to 5.0, 5.1, 5.2, 5.3, 5.4, 5.5, 5.6, 5.7, 5.8, 5.9 or 6.0, in particular pH of 5.5) 5% sucrose, 2 mM $MgCl_2$ and the elution of the vectors is carried out with a buffer with a greater ionic force comprising a polyol, notably a buffer of 650 mM NaCl, 20 mM Bis-Tris (pH 6), 5% sucrose, and 2 mM $MgCl_2$. The process according to the invention therefore advantageously allows a reduction in the amount of salts required for eluting the vectors from the column relative to the conventionally used salt concentration. According to a particular embodiment, the elution is carried out with a buffer comprising an NaCl concentration comprised between 450 mM and 1,000 mM. According to an alternative of this embodiment, the elution buffer contains between 450 and 800 mM of NaCl, between 2% and 8%, more particularly 5%, of a polyol (in particular sucrose), the buffer having a pH comprised between 5.5 and 6 (notably a Bis-Tris buffer optionally containing 2 mM $MgCl_2$).

According to another embodiment, the elution of the anion exchange chromatography substrate is carried out in two phases, with a first step corresponding to an applied pre-elution with a view to removing the contaminants of the production. The buffer of the first elution may for example comprise NaCl at a concentration comprised between 0 and 450 mM (notably between 0 and 350 mM if the buffer has a pH of less than or equal to 6, notably comprised between 5 and 6, more particularly a pH equal to 5.5 or 6.0, or between 0 and 450 mM if the buffer has a pH greater than or equal to 7). The second elution is then applied for recovering the virus (e.g. the viral vector) from the chromatography substrate. When the pH of the second elution buffer is comprised between 5 and 6, more particularly with a pH of 5.5, for example, the salt concentration may be comprised between 450 and 800 mM. When the pH of the second elution buffer is greater than or equal to 7, the salt concentration may be comprised between 600 and 1,000 mM.

According to a particular embodiment, comprising a single elution step for the anion exchange chromatography substrate, the following steps are applied:
i) loading on the anion exchange chromatography substrate the solution obtained at the end of the ultrafiltration step, said solution being notably:
    either at a pH comprised between 5.5 and 6, and comprising an NaCl concentration comprised between 0 and 200 mM;
    or at pH 7, the NaCl concentration being comprised between 0 and 350 mM; and
ii) elution of the virus, notably a viral vector, from the anion exchange chromatography substrate with a buffer:
    or at a pH comprised between 5.5 and 6, and comprising an NaCl concentration comprised between 450 and 800 mM;
    or at pH 7, the NaCl concentration being comprised between 600 and 1,000 mM.

According to another particular embodiment, comprising two elution steps for the anion exchange chromatography substrate, the following steps are applied:
i) loading, on the anion exchange chromatography substrate, the solution obtained at the end of the ultrafiltration step, the solution not comprising any added NaCl;
ii) a first elution of the anion exchange chromatography substrate (with the purpose of removing the contaminants), the first elution buffer being
    either at a pH comprised between 5.5 and 6, and comprising an NaCl concentration comprised between 0 and 350 mM;
    or at pH 7, the NaCl concentration being comprised between 0 and 450 mM; and
iii) a second elution of the anion exchange chromatography substrate (with the purpose of recovering the virus, notably the viral vector), the second elution buffer being:
    either at a pH comprised between 5.5 and 6, and comprising a NaCl concentration comprised between 450 and 800 mM;
    or at pH 7, the NaCl concentration being comprised between 600 and 1,000 mM.

For the evaluation of the fractions and for the selection of those that will be subsequently subjected to the purification process, the column may be equipped at the output with a chromatograph equipped with a 280 nm UV absorbance reader, with a conductivity meter, with a plotter and with a fraction collector.

An exclusion chromatography step is preferentially carried out immediately after the anion exchange chromatography step. The exclusion resin used has an exclusion size comprised between 300 and 1,000 kDa, notably between 500 and 800 kDa. According to a particular embodiment, the exclusion chromatography column used is defined by an exclusion size of 500, 700 or 800 kDa. Moreover, in a particular embodiment, the column used for this step comprises a multimode resin, notably a resin with dual functionality of exclusion gel and adsorption gel (by hydrophobic interaction as well as by a positive charge of the substrate). As such mention may be made of the column Capto Core 700 (GE Healthcare). In an embodiment, the chromatography gel is an incompressible substrate. The sample of enveloped viruses or vectors from anion exchange chromatography is loaded on the column, and then the formulation buffer is injected at a suitable rate, for example at a rate of 0.5 mL/minute. The fractions to be collected are determined at the column outlet by means of a 280 nm UV absorbance reader.

According to one aspect, the invention relates to a process for purifying enveloped viruses comprising an ultrafiltration/diafiltration step, notably a TFF, said step being carried out by means of buffers containing a polyol. The inventors were able to show that by adding a polyol in an ultrafiltration/diafiltration buffer it is possible to significantly increase the yield of purification (Table 2 below, in the examples), which has never been reported. The polyols which may be used during this step and their concentrations are specified below. The buffers used during the ultrafiltration step and during the diafiltration step may either be different or identical. In a particular embodiment, the ultrafiltration step is carried out by means of a buffer having a pH of about 7 (notably a pH comprised between 6.8 and 7.2 (for example equal to 6.8, 6.9, 7.0, 7.1 or 7.2), more particularly a buffer of pH 7) and diafiltration is carried out by means of a buffer having a pH of less than 6, or comprised between 4.5 and 6.2 (notably equal to 4.5, 4.6, 4.7, 4.8, 4.9, 5.0, 5.1, 5.2, 5.3, 5.4, 5.5, 5.6, 5.7, 5.8, 5.9, 6.0, 6.1 or 6.2), notably a pH comprised between 5 and 6, more particularly a buffer with a pH comprised between 5.5 and 6 (notably equal to 5.0, 5.1, 5.2, 5.3, 5.4, 5.5, 5.6, 5.7, 5.8, 5.9 or 6.0), more particularly a buffer with a pH equal to 5.5 or 6, in particular a buffer with a pH equal to 5.5. Tangential flow filtration may be carried out by means of a membrane with hollow fibers or a planar membrane or spinal wound membrane cassette, whose pore exclusion size is comprised between 300 and 800 kDa, in particular between 500 and 750 kDa. According to another embodiment, the pore exclusion size is of at least 300, 400, 500, 600, or 700 kDa, or is of 800 kDa. According to a preferred embodiment, the membrane used for the tangential flow filtration is characterized by a pore exclusion size of 750 kDa. According to a particular embodiment, at the end of the ultrafiltration/diafiltration step, the enveloped viruses, notably the enveloped viruses present in the filtrate of a clarification step, are concentrated up to the minimum possible volume, for example at least 5×, at least 10×, 15×, 20×, 25×, 30×, 35×, 40×, 45×, 50×, 55× or 60×. For example, the enveloped viruses are concentrated 36.6× or 50× at the end of the ultrafiltration/diafiltration step. According to another embodiment, the ultrafiltration/diafiltration step allows a reduction in the load of contaminants by more than 70%, 80%, 85%, 90% or more than 95%. According to a particular embodiment, the ultrafiltration/diafiltration step is carried out in the following way: a first concentration is achieved, for example a concentration of 25× (notably, by passing from a volume of 500 mL to a volume of 20 mL), followed by diafiltration with at least 2, 3, 4, 5, 6, 7, 8, 9, or even at least 10 volumes of an acid buffer either containing or not a polyol and/or one or several antioxidants, for example with 10 volumes of buffer; this step is then followed by a second concentration step, notably up to the minimum possible volume, in order to attain for example a concentration of 50×.

The ultrafiltration/diafiltration step may be followed or preceded with an anion exchange chromatography step, or followed by an exclusion chromatography step according to the conditions described in detail above.

According to a particular embodiment, the purification process is intended for the production of enveloped viruses of research grade. In this case, the ion exchange chromatography step may be omitted (the process then comprises for example the steps (a), (b) and (d) described above). According to another embodiment, the process is intended for purifying clinical grades of viruses. In the latter case, the anion exchange chromatography step is preferably included. Moreover, the exclusion chromatography step may be followed by a sterilizing filtration step, notably by means of a filtering membrane, in particular a membrane with a retention threshold of less than or equal to 0.22 μm.

In the context of the present invention, the term "polyol" defines a linear, cyclic or bicyclic carbonaceous molecule comprising between 3 and 18 carbon atoms, in particular between 3 and 12 carbon atoms, substituted with at least 3-6 hydroxyl groups, in particular 8 hydroxyl groups. The polyol may for example be an aldose or ketose monosaccharide, notably a tetrose, a pentose or a hexose. Mention may notably be made of the following monosaccharide polyols: erythrose, threose, ribose, arabinose, xylose, lyxose, allose, altrose, glucose, mannose, gulose, idose, galactose, talose, erythrulose, ribulose, xylulose, fructose, psicose, sorbose, and tagatose. The polyol may also be selected from the following disaccharides or trisaccharides which form a non-limiting list of other polyols which may be used in the implementation of the invention: cellobiose, gentiobiose, inulobiose, isomaltose, isomaltulose, kojibiose, lactose, lactulose, laminaribiose, leucrose, maltose, maltulose, melibiose, nigerose, robinose, rutinose, sucrose, sophorose, trehalose, trehalulose, turanose, erlose, fucosyllactose, gentianose, inulotriose, 1-kestose, 6-kestose, maltotriose, mannotriose, melezitose, neokestose, panose, raffinose, and rhamninose. In a particular embodiment, the polyol is selected from among raffinose, isomaltotriose, sucrose, mannitol, sorbitol, trehalose, glucose and glycerol. In a particular embodiment, the polyol is sucrose.

The polyol concentration may vary to a great extent, and may in particular be different for each of the different buffers applied during this step. The polyol concentration may notably be comprised between 1% and 15% (w/v) notably between 1.5% and 10%, in particular between 2% and 8%, more particularly between 2% and 5%. In a particular embodiment, the polyol concentration of one or several of the buffers of anion exchange chromatography is 5% (w/v). In a particular embodiment, all the buffers used during the purification process comprise a polyol, notably sucrose, in particular at 5% (w/v). Thus, according to this embodiment, the process may comprise a TFF step, an anion exchange chromatography step and an exclusion chromatography step during which all the buffers used comprise a polyol. In another embodiment, the buffers of the TFF steps and of anion exchange chromatography comprise a polyol while the buffers used for equilibrating and eluting the exclusion chromatography column do not comprise any polyol. These buffers correspond to the formulation buffer of which the composition will depend to a large extent on the therapeutic destination and on the method for administering the finished product.

In another embodiment, one or several of the buffers used during the process of the present invention, notably the buffers used during the ultrafiltration/diafiltration and/or the anion exchange chromatography, comprise a magnesium salt, notably magnesium chloride or magnesium sulfate. The magnesium salt concentration, in particular magnesium chloride or magnesium sulfate in each of the buffers may, independently for each buffer, be comprised between 0.1 mM and 5 mM, notably between 1 and 3 mM, in particular 2 mM.

In another embodiment, one or several of the buffers used during the process of the present invention comprise L-His, L-Met, L-Cys, glutathione, or vitamin C with a view to inactivating free radicals. The concentration of these components in each of the buffers may, independently for each buffer, be comprised between 0.1 mM and 20 mM.

The purification process according to the invention may also comprise one or several steps of treating the sample(s) with a nuclease, notably a benzonase. The nuclease may be used before or after each of the steps. In an embodiment, the nuclease, in particular the benzonase, is used in the culture medium of the producing cells after the plasmid transfection step.

According to an embodiment, one or several steps of the purification are carried out at a temperature below room temperature, in particular at a temperature comprised between 2 and 12° C., more particularly between 4 and 10° C. According to a particular embodiment, one, several or all the steps of the purification are carried out at about 4° C.

According to an embodiment, the enveloped virus purified according to the methods of the present invention is an enveloped recombinant virus. Preferably, the enveloped virus is a pseudotyped recombinant retrovirus, more particularly a lentivirus, in which the envelope protein is derived from the GaLV virus (in particular the modified GaLVTR glycoprotein for lentiviral vectors), from the VSV virus (in particular the VSV-G envelope) or from the measles virus (MV). In a particularly preferred alternative, the enveloped virus purified according to the method of the present invention is a pseudotyped recombinant retrovirus, more particularly a lentivirus, in which the envelope protein is derived from the GaLV virus (in particular the modified GaLVTR glycoprotein for lentiviral vectors).

LEGEND OF THE FIGURES

FIG. 1. Two processes for purifying LV-GaLV-TR lentiviral particles: process (A) is a simplified process of applying a single exclusion chromatography step (gel filtration) after the step of tangential flow filtration; and process (B) is a more elaborate process aimed at obtaining a higher purity than during the use of process (A), for example, with the aim of producing vectors for clinical use.

Figure 2:
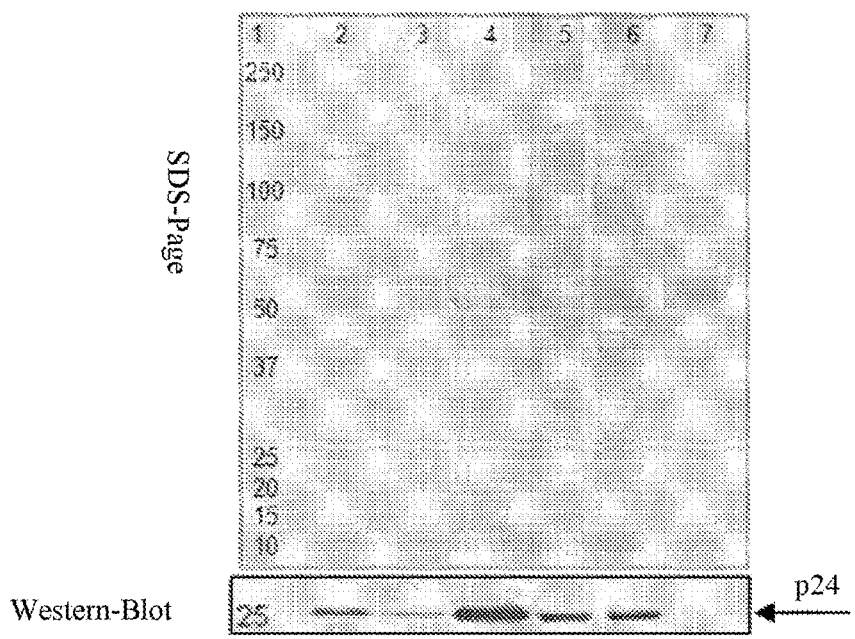

FIG. 2. Comparison of the membranes with cutoffs of 500 kDa and of 750 kDa in the removal of contaminating proteins (SDS-PAGE (at the top) and Western blot anti-p24 (at the bottom)). The 24/25 kDa band (=p24) is well visible for all the samples on the Western blot: 1) size markers; 2) diafiltration (a) (test 1) at 750 kDa; 3) diafiltration (b) (test 2) at 750 kDa; 4) ultracentrifugation at 68,338 g for 3 h (resuspension in a culture medium X-vivo 20); 5) diafiltration (a) (test 1) at 500 kDa; 6) diafiltration (b) (test 2) at 500 kDa; 7) culture supernatant containing LV-GaLV-TR vectors.

Figure 3:
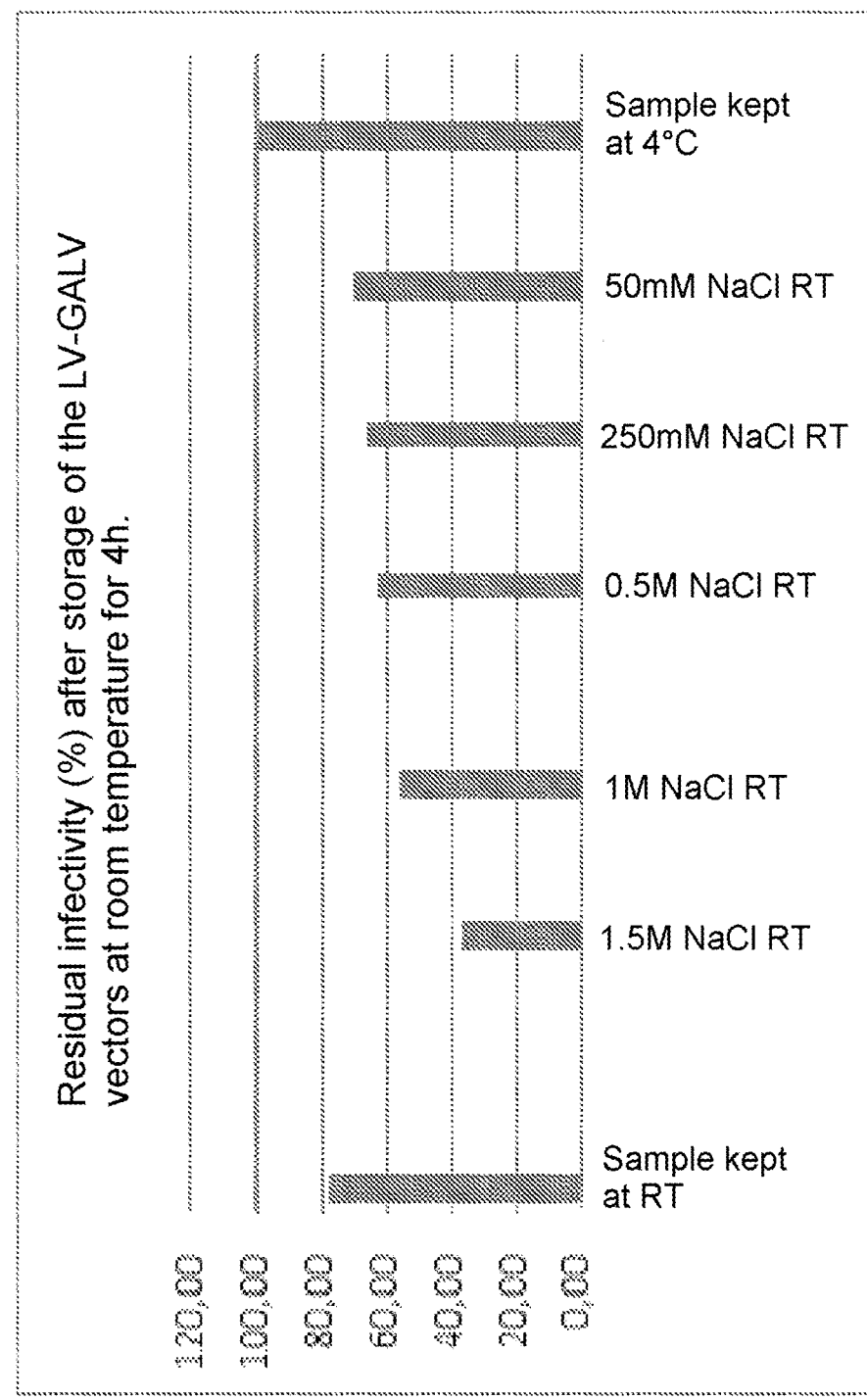

FIG. 3. Effect of NaCl on the stability of the LV-GaLV-TR vectors coding for a GFP, stored at room temperature. The vectors are incubated for 4 hours at a pH of 7.0 (PBS) at room temperature (RT). In order to optimize the anion exchange chromatography step, we tested the stability of the vectors in a saline NaCl medium. For this, the vectors were incubated after the UF/DF step in PBS buffers of pH 7.0 with different NaCl concentrations for 4 h at room temperature. Next, the vectors were titrated on HCT116 cells. 48 hours later, the cells are passed on FACS (flow cytometry) in order to measure the expression percentage of GFP.

Figure 4:
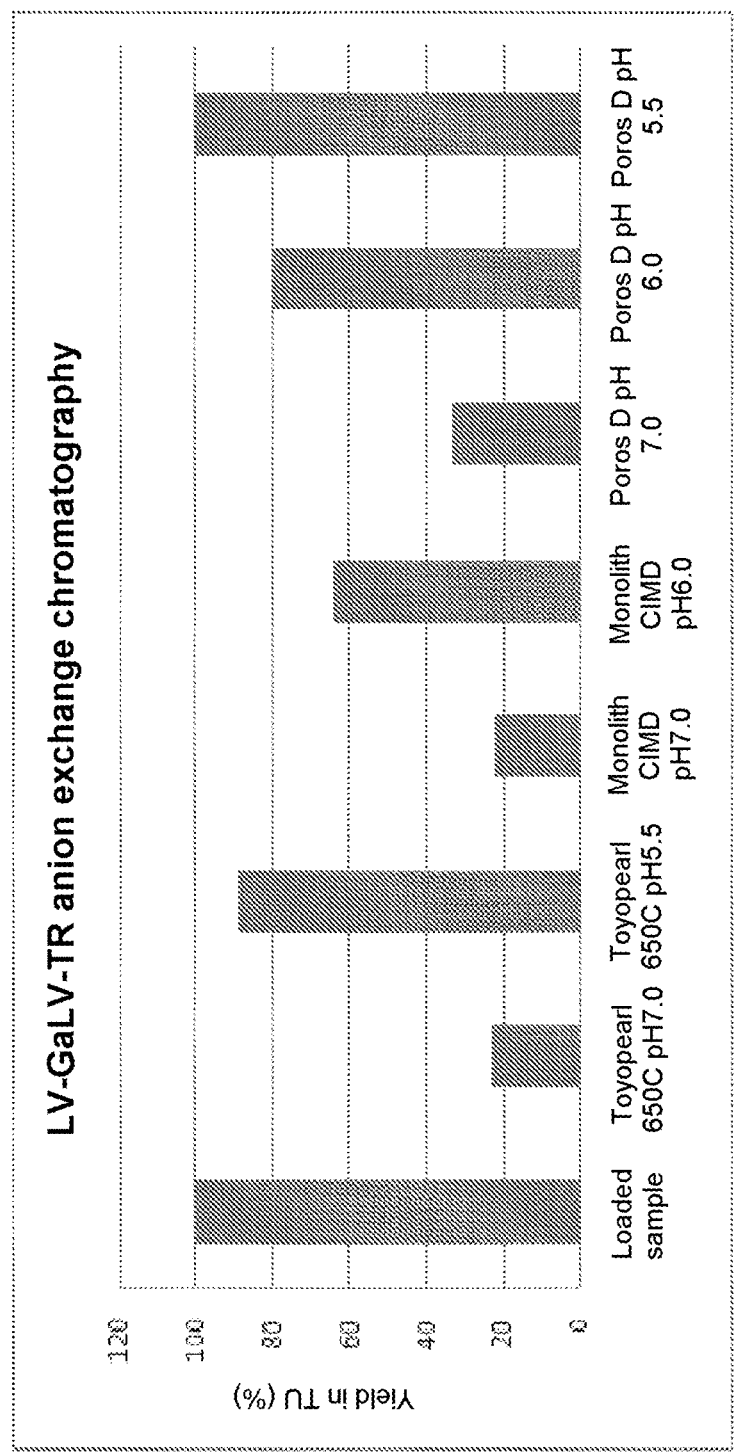

FIG. 4. Effect of the pH and of the salinity of the elution buffer on the purification yield of the infectious lentiviral vectors after an anion exchange chromatography step. The preparation of vectors was produced by transfection of HEK293T cells, clarified and concentrated/diafiltered by TFF with a view to being used for evaluating various substrates of anion exchange chromatography (low). Various substrates were evaluated: Toyopearl 650C DEAE, CIM D (DEAE) and Poros D. The yield of 100% is equivalent to the infectious titer after the preceding TFF step.

Figure 5:
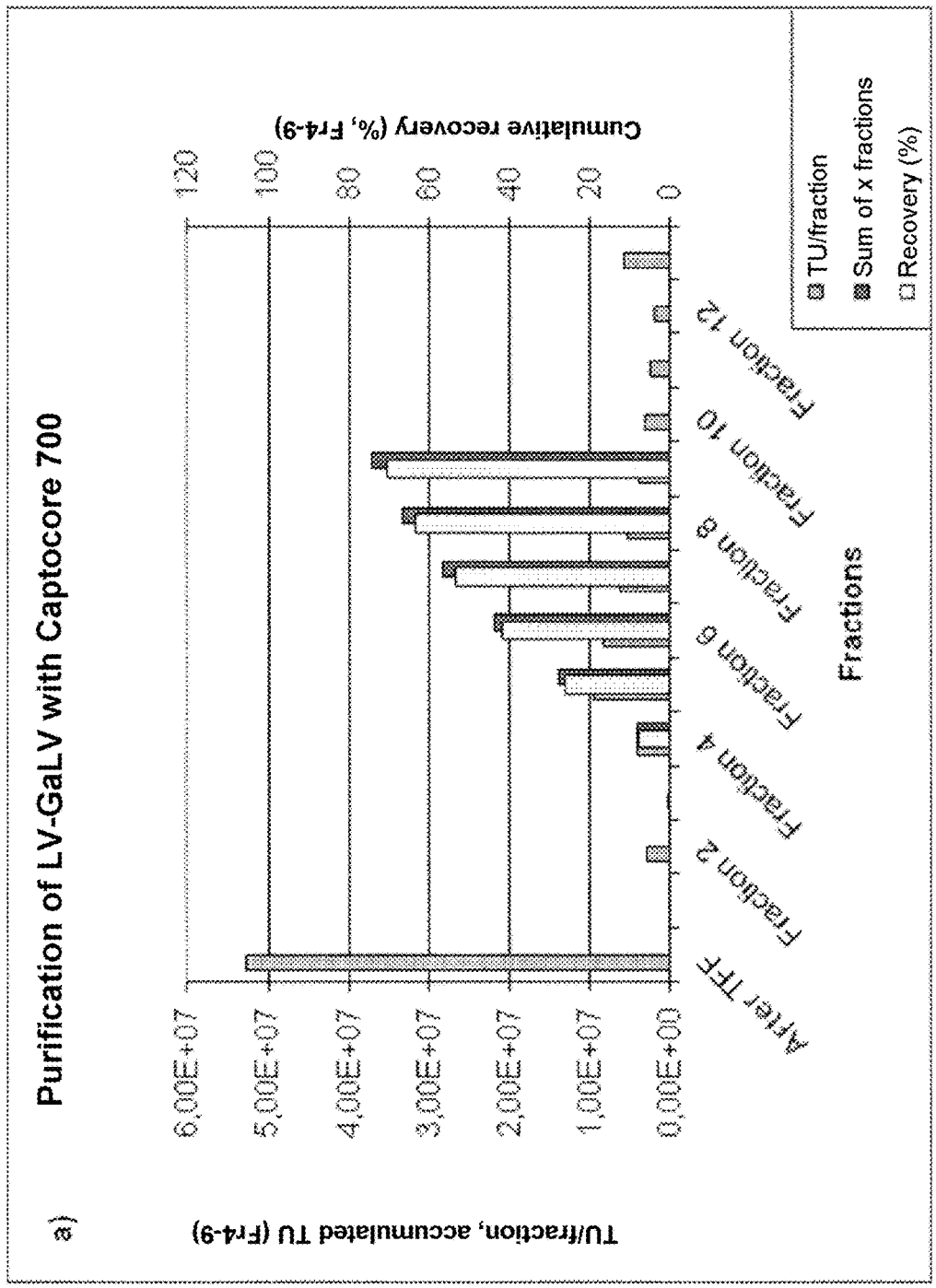
Figure 5:
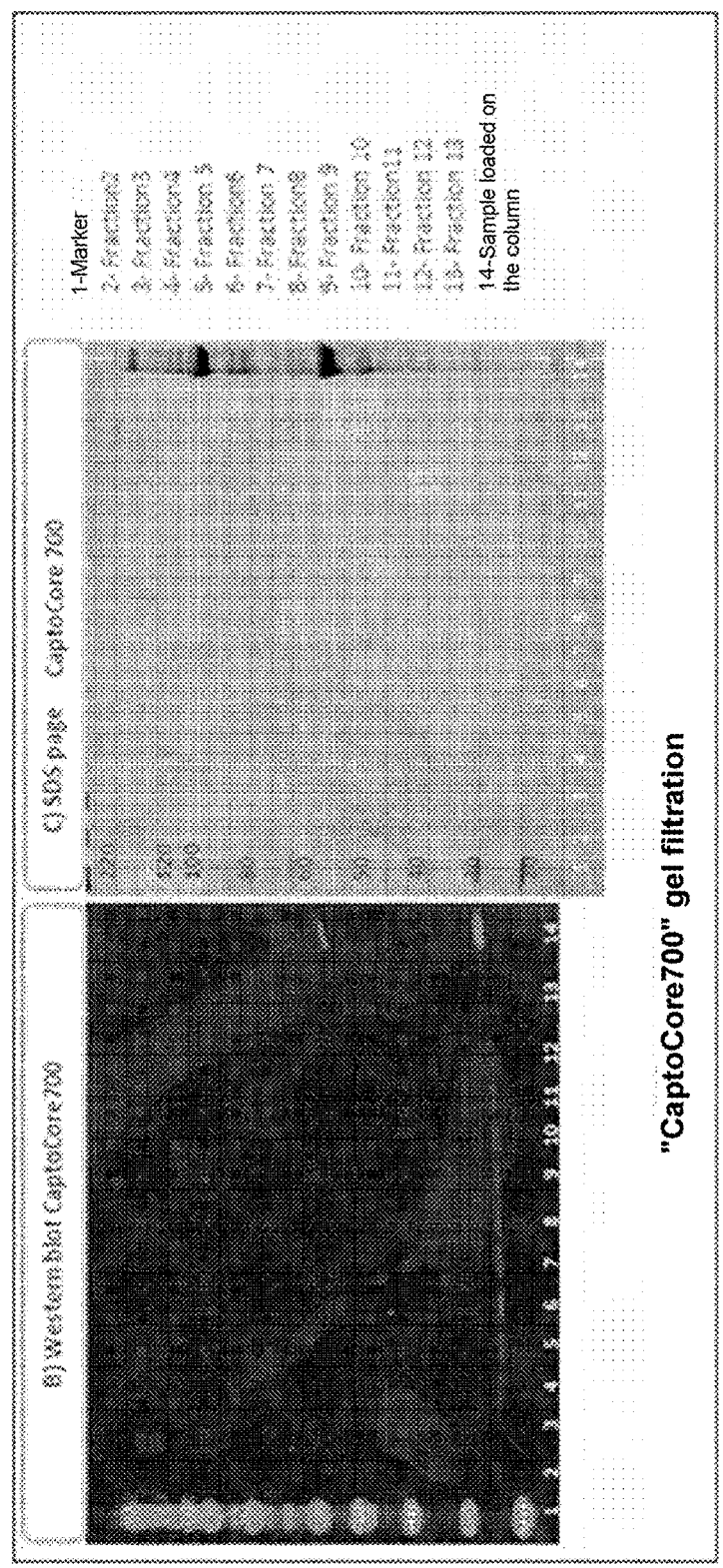

FIG. 5. Purification of a preparation of GaLV-TR lentiviral vectors by exclusion chromatography (Capto Core 700). Three mL of a lentiviral preparation were concentrated/diafiltered and then passed over a column of Capto Core 700 (4.5 mL). A PBS buffer (pH 7.0), 5% sucrose, and 2 mM $MgCl_2$ were used during this step for equilibration of the column and of the formulation. 1 mL fractions were harvested and analyzed for vector concentration (TU): a) Chromatogram showing the titer (TU) by fraction, the accumulation of the vector amount for the fractions 4-9 and accumulative recovery (%) for the fractions 4-9; b) Western blot of all the fractions; c) SDS-PAGE of all the fractions.

Figure 6:
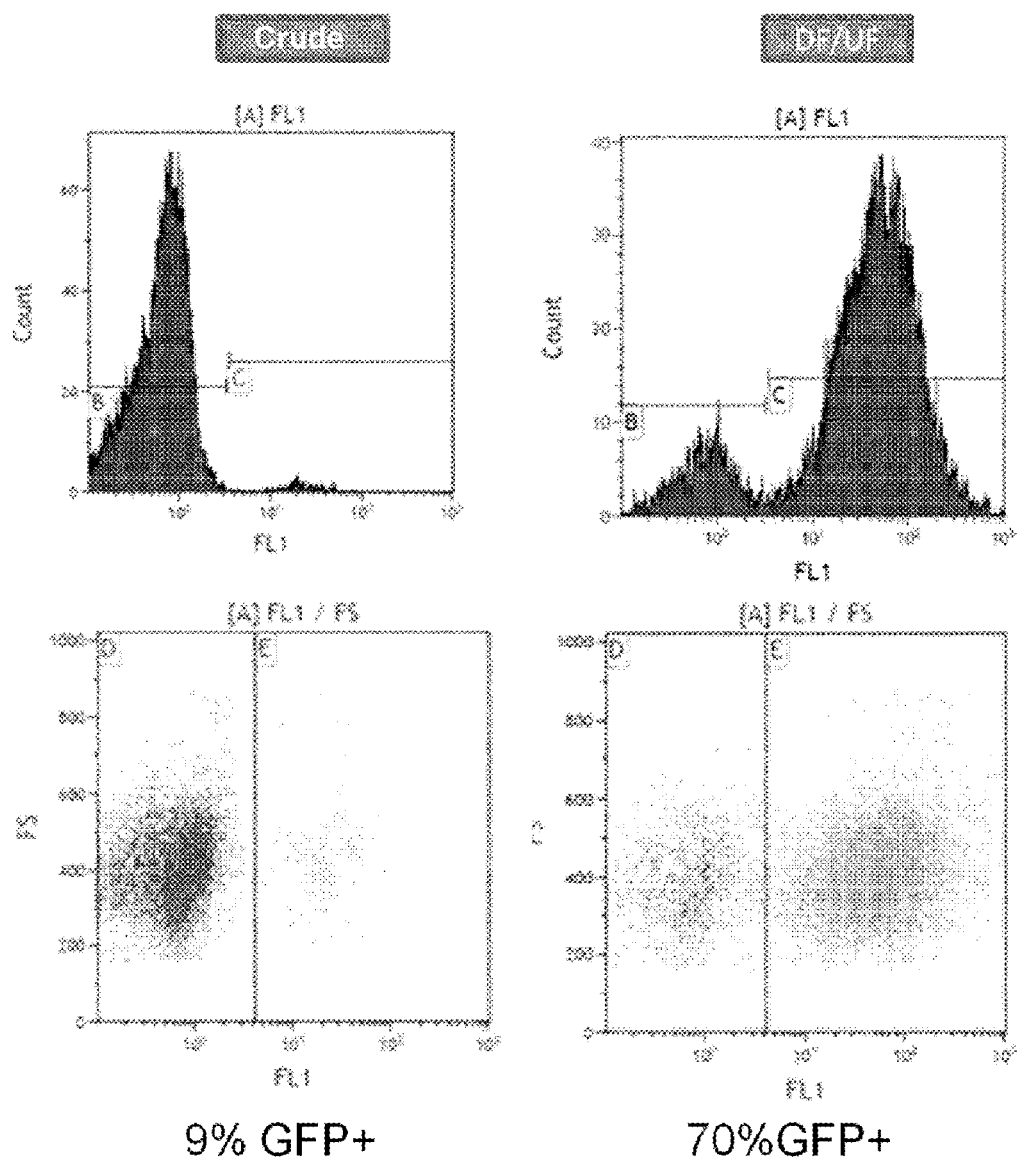

FIG. 6. Transduction of the CD34+SC cells (blood from the umbilical cord) with an HIV-GaLV-TR vector from MOI 20.

Crude: percentage of cells expressing the GFP determined by flow cytometry of the CD34+ cells transduced with the crude product HIV-GaLV-TR.

DF/UF: percentage of cells expressing the GFP determined by flow cytometry of the CD34+ cells transduced with the preparation of HIV-GaLV-TR vectors obtained after purification and concentration by TFF of the crude product.

EXAMPLES

The studies reported in the present application benefited from a subsidy via the $7^{th}$ Framework Program of the European Community (FP7/2007-2013), under number 222878.

Materials and Methods

Cells:

The HEK293T and HCT116 cell lines (colorectal cancer cells CCL-247, origin: ATCC) are cultivated at 37° C., with 5% $CO_2$ in Dulbecco's modified Eagle's medium (Gibco) (DMEM+Glutamax) supplemented with 2 to 10% of fetal calf serum (FCS) (Life Technologies). Culture medium: DMEM/FCS buffered at pH 6.0 by adding hydrochloric acid (HCl 37%, Sigma-Aldrich), and then filtered by means of a Corning® 1,000 mL filter (0.22 µm PES (polyethersulfone)).

Production of Viral Vectors:

Viral vectors derived from HIV-1, pseudotyped with various glycoproteins are produced by transient quadri-transfection with calcium phosphate in 293T cells, by 4 plasmids as described by Merten et al. (2011). $2 \times 10^8$ 293T cells are sown in a 1,760-$cm^2$ Hyperflask (Corning) in 550 mL of DMEM 10% FCS (Kutner et al. 2009). 24 hours later, the culture medium is replaced with the transfection medium, by combining therein the DNA/$CaCl_2$/HBS complex. The 4 plasmids: gagpol (pKLgagpol) 136 µg, rev (pKrev) 52.25 µg, the transgenic plasmid (pCCL-eGFP) 206.8 µg, the suitable envelope plasmid for each pseudotype: GaLV-TR: pBA.GALV-TR/Ampho-Kana (Gibbon ape Leukemia Virus) 223 µg for generating LV-GaLV-TR; VSV-GpMDG (Vesicular stomatitis virus-g) 68.13 µg for generating LV-VSV-g; pFΔ30 and pHCMH2 (modified envelope proteins of the measles virus) 40 µg and 14 µg for generating the LV-MV; a sufficient amount for 18 mL of $H_2O$ and 8.9 mL of TE0.1x, mixed with 3 mL of $CaCl_2$ (2.5M) and then add 30 mL of HBS2x, await the formation of the complex for 4 min and add the mixture to the culture medium. After 16 hours, the supernatant is replaced with fresh medium of 2% FCS 15U Benzonase (Merck) and 2 mM of $MgCl_2$ (Sigma-Aldrich). The harvest is made after 48 hours post-transfection; the supernatant is filtered on a 0.45 µm filter in cellulose acetate (CA) 1 L (Corning).

The retroviral vectors MLV-GaLV are produced by PG13 cells. These are cells producing MLV-GaLV vectors (Miller et al. 1991). The cells are maintained in Dulbecco's modified Eagle's medium (Gibco) (DMEM+Glutamax) supplemented with 2 to 10% of FCS, at 37° C., 5% of $CO_2$. The harvesting of the vectors is made after 24 hours of having changed the culture medium. Next, the production supernatant is clarified on a 0.45 μm filter in cellulose acetate (Corning).

Concentration of the Viral Vectors by Tangential Flow Filtration (TFF):

This step consists of concentrating the production supernatant and then replacing the culture medium with an adequate buffer for the continuation of the process.

Ultrafiltration (UF) is carried out after the preparation of the UF cassette and the determination of the permeability normalized to water NWP at 0.5 bars at 20° C. The membrane is then equilibrated with a Bis-Tris buffer at pH 6.0, 5% sucrose, and 2 mM $MgCl_2$ or with other buffers with a view to carrying out concentration/diafiltration at other pHs (for example: PBS, pH 7.0, 5% sucrose and 2 mM $MgCl_2$). The whole process is carried out at about 4° C. and the tank of the product to be concentrated is put in an ice box.

Principle: A first concentration up to a volume of 20 mL followed by diafiltration with 10 volumes of buffer for loading ion exchange chromatography (in this case: 10×20 mL) are carried out. These steps are followed by a second concentration down to the minimum possible volume (10 mL in the present case).

Membrane 750 kDa, 410 $cm^2$: "Hollow fiber cartridge" (GE Healthcare, Ref: UFP750-E3MA) by using the Kros-Flow Research II TFF system (Spectrum).

After validation of the integrity of the membrane, the concentration of the vectors begins with an initial volume of 500 mL of crude supernatant and is concentrated by the membrane from 500 mL to 20 mL.

The concentrated product is diafiltered against 200 mL of Buffer A (with a view to diafiltering 10 times 20 mL of concentrate). This represents a concentration factor of 25×. The final volume of the diafiltrate is 10 mL. In this case, the concentration factor is 50×.

Anion Exchange Chromatography:

In a first procedure, the anion exchange chromatography step is carried out downstream from the TFF. Several chromatography substrates are tested: monolithic column CIMD DEAE, CIMD Q (BIA Separations, Villach, Austria), volume of the column: 1 mL; Sartobind D 75MA, volume: 2.1 mL (Sartorius Stedim Biotech); Poros PI, volume of the column: 4 mL; Poros D 50, volume of the column: 4 mL; Poros HQ, volume of the column: 4 mL (LifeTechnologies); Toyopearl 650C DEAE, volume of the column: 2 mL (Tosoh).

The column to be tested is connected to a Biologic-LP chromatograph (Bio-Rad) equipped with a 280 UV absorbance reader, with a conductivity-meter, a plotter (Chart recorder 1327, Bio-Rad), and a Fraction collector (Model 2110, Bio-Rad).

The column is equilibrated with 5 column volumes (5 CV) of buffer A at 2 mL/min. After loading the sample on the column, the column is washed with 5 CV of a suitable equilibration buffer (depending on the desired pH, according to table A). An elution in two steps is then carried out: 0.3 M of NaCl, 20 mM of Bis-Tris, 5% sucrose, 2 mM of $MgCl_2$ (pH 6.0) and then 650 mM of NaCl, 20 mM of Bis-Tris, 5% sucrose, 2 mM of $MgCl_2$ (pH 6.0) for eluting the vectors. Three other pHs are tested, pH 5.5, 7.0 and 8.0, by using the suitable buffers (including buffers such as bis-propane, PBS, L-His), in the presence (5%) and in the absence of 5% sucrose and of $MgCl_2$ (2 mM).

Finally, the fraction is loaded straightaway on the gel filtration column (exclusion chromatography) for removing the contaminating salts and proteins eluted with the vectors at 650 mM of NaCl.

In a second procedure, the clarified production supernatant is loaded on an anion exchange chromatography column Poros D, without any preliminary ultrafiltration/diafiltration step in order to evaluate the yield of the chromatography under these conditions. The equilibration buffer used has a pH of 5.5, and contains 5% sucrose and 2 mM of $MgCl_2$.

Exclusion Chromatography:

This is the final step before the sterilizing filtration for processes A and B (FIG. 1). This step consists of removing the contaminants having a size of less than that of the gel used (for example, 750 kDa, or else 500 kDa). The Capto Core 700 column was used for this step. This is a gel with dual functionality: exclusion chromatography and adsorption gel chromatography.

Before beginning the loading, the column is sanitized with NaOH 1M and equilibrated with the formulation buffer. The UF/DF product (process A), or the fractions corresponding to the chromatography peak of anion exchange chromatography (AXC) (process B) is loaded on the column. 8 mL (UF/DF or AXC fraction) are loaded with a flow rate of 0.5 mL/min. Next the formulation buffer is injected with 0.5 mL/min (5 CV of formulation buffer). The fraction corresponds to the UV peak, is collected (about 16 mL) and then filtered on a 0.22 μm filter (sterilizing filtration). The samples are stored at −80° C.

Titration of the Viral Vectors:

The viral titer in transduction units (TU) of the vectors having the reporter gene eGFP, is analyzed by transduction of HCT116 cells. 72 hours after transduction the cells are passed to FACS for determining the titer in TU/mL as described earlier (Pfeifer et al. 2009). For physical analysis of the viral particles, the kit ELISA p24 (PerkinElmer) was used for quantifying the capsid protein of the lentiviruses p24 according to the instructions of the supplier.

Transduction of CD34+ Blood Cells of the Umbilical Cord:

The CD34+ cells are isolated from blood from the umbilical cord by immunomagnetic selection (Miltenyi Biotec). The cultivation and the transduction of the CD34+ cells is accomplished as described (Charrier et al. 2011): first the cells are pre-stimulated overnight in a medium X-Vivo 20 (Lonza) and supplemented with cytokines. The pre-activated cells are sown in a 48-well plate ($5 \times 10^4$ cells/100 μl). The transduction is accomplished by adding 100 μl of vectors ($10^6$ TU) purified in the presence of 8 μg/mL of vectofusine-1 (Fenard et al., 2013). After 6 hours of incubation, 1 mL of differentiation medium (X-VIVO-20 supplemented with 10% serum, and in the presence of cytokines (hSCF, h-Il-3 h-Flt3 h-Il-6) as described (Charrier et al. 2011)) is added into each well, and after 5 days, the transduction efficiency is evaluated by measuring the expression of GFP by FACS (FC500, BD Biosciences).

SDS-PAGE Western Blot:

The culture samples containing lentiviral vectors or purified samples are analyzed with SDS-PAGE and by Western blot in order to detect the presence of p24 capsid proteins. The revealing of the p24 proteins is carried out according to the method developed by LI-COR, with the Odyssey apparatus and the Odyssey 2.1 software package. The primary antibody used is an anti-p24 (Santa Cruz # SC-57823) for detecting p24 capsid proteins of HIV. The antibody is used with a dilution of 1/200 in 0.1% PBS1x-Tween+blocker Odyssey (1:1). The secondary goat antibody used coupled with the fluorochrome "Dye 800" of Li—COR is directed against the primary antibodies.

Quantification of the Residual Proteins and of the Specific Residual DNA:

The total proteins are quantified by Bradford's method (Bio-Rad) with serum albumin as a standard. The test is conducted according to the instructions of the supplier.

Residual DNA: the quantification of residual DNA of plasmid origin and/or stemming from the host cell is accomplished by quantitative PCR. The samples are treated with proteinase K (Roche) and then the DNA is extracted by using the system: MagNA Pure DNA and viral NA small volume kit (MagNA Pure 96 Roche). Quantitative real time PCR is then carried out, with specific primers for the gene of kanamycin in order to detect residual DNA of plasmid origin. In order to detect the residual DNA from the host cell, primers are used which target the E1A gene. Absolute quantification is carried out relative to a reference plasmid containing the regions amplified by quantitative PCR and for which the number of copies is known.

TABLE A buffers used during the process

| Buffers | | pH | Sucrose (Sigma-Aldrich) | $MgCl_2$ (Sigma-Aldrich) |
|---|---|---|---|---|
| buffer A | L-Histidine 20 mM (Sigma-Aldrich) | 5.0 | 5% W/V | 2 mM |
| buffer B | Bis-Tris 20 mM (Sigma-Aldrich) | 5.5 | | |
| buffer C | Bis-Tris 20 mM (Sigma-Aldrich) | 6 | | |
| buffer D | PBS (GIBCO ®) | 7.2 | | |
| buffer E | Bis-Propane 20 mM (Sigma-Aldrich) | 8 | | |

Results

This invention relates to the development and the establishment of a novel purification protocol for lentiviral vectors derived from HIV-1 or from other retroviruses produced by transient transfection or with stable and pseudotyped producing cells with different envelope glycoproteins, such as GaLV-TR, VSV-G, measles virus and γ-retroviral vectors GaLV produced from stable cells, such as PG13, while ensuring a good yield and good quality of the purified viral particles. This development is essentially, but not exclusively, based on three purification techniques: TFF (tangential flow filtration), anion exchange chromatography and exclusion chromatography. The different combinations are illustrated in FIG. 1.

Cultivation of Cells and Clarification:

These steps consist of producing retroviral and lentiviral vectors by using stable cells such as PG13 characterized by a stable and continuous production of retroviral vectors in a continuous cultivation with a regular exchange of medium and with cells such as HEK293 or HEK293T which have to be transfected with 3 or 4 plasmids (providing the 'helper' functions of the lentivirus and the sequence of the recombinant vector) with a view to inducing the production of lentiviral vectors. Transient production is limited in time and allows one or several harvests a few days after transfection. The titers generally depend on the construction (sequence) of the vector but also on the envelope protein. The following titers may be obtained with these production systems (Table 1).

TABLE 1

Concentrations of vectors obtained with the different production systems:

| Production cell, pseudotype vector | Vector concentration (TU/mL, gi/mL) | References |
|---|---|---|
| PG13, MLV-GaLV-TR | $5 \times 10^6$ TU/mL | Miller et al. 1991 |
| HEK293T, LV (HIV-1) - GaLV-TR | $5 \times 10^5$ TU/mL | Sakuma et al. 2010 |
| HEK293T, LV (HIV-1) - VSVg | $1\text{-}5 \times 10^7$ TU/mL | Merten et al. 2011 |

Before any further treatment, it is possible to remove the cell debris and the aggregates present in the supernatant of the production. Conventionally, a 0.45 μm filter (cellulose acetate) is used. The yield of this step is of 80±5%. However, one skilled in the art may use other membranes or cascades of membranes, characterized by a similar behavior and yield.

Tangential Flow Filtration:

Tangential flow filtration comprises two successive steps of ultrafiltration and diafiltration (UF/DF). Both of these steps give the possibility of removing a great portion of the contaminants of which the size is less than the exclusion size of the pores of the membrane used. This UF/DF step also gives the possibility of concentrating the viral particles and of reducing the volume of the product to be purified. A membrane of 110 $cm^2$ with a pore exclusion size of 750 kDa (GE Healthcare) was used. In order to begin UF, different concentrations of sucrose (notably 5% of sucrose (weight/volume)) and various concentrations of $MgCl_2$ (notably 2 mM of $MgCl_2$ (final concentration)) are added to the clarified product. Next the UF concentration step is performed with a flow of 80 mL/mn, 7 psig. The TFF tank is placed in an ice box in order to ensure low temperature during UF/DF. The diafiltration step begins after having reduced the volume from 500 mL to 20 mL during UF. For DF, 200 mL (10 volumes of the concentrated product) of the diafiltration buffer (PBS, 5% sucrose, 2 mM $MgCl_2$) are used. At the end of this step, 20 mL of UF/DF product are recovered in a 50 mL Corning tube. The selection of the buffer depends on the use of the preparation or on the optimum conditions of the step following concentration/diafiltration (e.g., in this case, other buffers may be used like Bis-Tris (pH 6.0), 5% sucrose, 2 mM $MgCl_2$; see Table A). The samples are titrated on HCT116 cells as described by Fenard et al. (2013).

Studies for Optimization of the Concentration/Diafiltration Conditions:

1. The lentiviral particles have a diameter ranging from 80 to 120 nm meaning that the pore size of membranes which may be used for the concentration/diafiltration may range at most up to about 50 nm (or 750 kDa). Within the scope of this invention, the cutoff sizes of 500 kDa and 750 kDa were evaluated. The yields (in TU) were the following: 64% for the 750 kDa membrane versus 34% yield in TU for the 500 kDa membrane.

FIG. 2 shows electrophoresis gels (SDS-PAGE and Western blot) for the preparation of vectors after tangential filtration by using membranes with cutoffs of 500 kDa and 750 kDa. In addition to the higher yields obtained upon using 750 kDa membranes, it is clear that a cutoff of 750 kDa has a positive effect (FIG. 2, columns 2, 3) compared with the use of the 500 kDa membrane as regards the removal of contaminating proteins (FIG. 2, columns 5, 6). Further, the concentrate generated with the 750 kDa membrane contains bands of proteins much less intense than observed for the crude supernatant.

2. Given that the tangential filtration step is characterized by the generation of shearing fields leading to the inactivation of the retroviral/lentiviral particles, it was necessary to optimize this step with a view to maintaining the functionality of these vectors. The addition of a polyol at various concentrations was evaluated with a view to protecting the lentiviral vector from the adverse conditions of tangential filtration.

TABLE 2

Concentration/diafiltration yield of LV-GaLV-TR by using various concentrations of sucrose.

| | Yield % (TU) |
|---|---|
| 0% sucrose | 50.83 |
| 2% sucrose | 80.31 |
| 5% sucrose | 80.40 |
| 10% sucrose | 52.37 |
| 15% sucrose | 68.49 |

Note:
190 mL of crude supernatant were concentrated to 17 mL and diafiltered several times with PBS (pH 7) + various % of sucrose and 2 mM of $MgCl_2$.

These results clearly show the benefit of carrying out the concentration/diafiltration of supernatant containing LV-GaLV-TR vectors in the presence of sucrose and $MgCl_2$. The best yields are obtained at concentrations from 2% to 5% of sucrose (Table 2).

Further, the use of a moderate sucrose concentration has the advantage that the sample to be concentrated is less viscous since high sucrose concentrations (10%-15%) lead to an increase in viscosity.

3. Evaluation of the pH and its effect on tangential filtration and yield of functional vectors:

In the application FR 13 58909 filed by the present applicant, it was shown that the production of enveloped vectors pseudotyped with different envelope proteins is increased upon the use of a pH of 6.0 (up to 2×). It was decided to evaluate the impact of the selection of the pH of the supernatant containing the lentiviral vectors on the efficiency of the tangential filtration. In this context, two different pHs were evaluated (pH 6 and pH 7) during the concentration/diafiltration of the GaLV-TR pseudotyped lentiviral vectors (Table 3). The reduction of the pH from 7.0 to 6.0 led to a reduction of the yield by about 10% (from 73.6% to 64%). This yield however remains acceptable and it is therefore possible to envision concentration/diafiltration with an acid pH.

TABLE 3

Impact of the pH of the supernatant to be concentrated/of the diafiltration buffer on the concentration/diafiltration yields of GaLV-TR and VSV-g pseudotyped lentiviral vectors.

| Tangential filtration condition | LV vector | Yield (%, TU) |
|---|---|---|
| PBS, 5% sucrose 2 mM $MgCl_2$, pH 7.0 | LV-GaLV-TR | 73.64 |
| Bis-Tris 20 Mm, 5% sucrose, 2 mM $MgCl_2$, pH 6.0 | LV-GaLV-TR | 63.99 |

4. Identification of the best condition for concentration/diafiltration of GaLV-TR lentiviral vectors:

As regards the GaLV-TR lentiviruses, the best concentration/diafiltration (tangential filtration) condition was the following: the LV-GaLV-TR vectors (1 L) are clarified through a 0.45 μm cellulose acetate membrane, in the presence of 5% sucrose and 2 mM $MgCl_2$, followed by the TFF step (cartridge 750 kDa, 410 $cm^2$) with reduction of the volume to be reached of 20 mL (50×). A diafiltration step is then carried out against a volume of 200 mL of suitable buffer (for example, Bis-Tris 20 mM, pH 6.0, 5% sucrose and 2 mM $MgCl_2$ or PBS, pH 7.0, 5% sucrose and 2 mM $MgCl_2$).

The yield of this step for LV-GaLV-TR vectors is 86%±5% for an initial volume of 550 mL of crude product. The volume of the concentrated product is 15 mL with a concentration factor of 36.6× and the removal of the contaminants attained more than 90%.

5. Evaluation of the established tangential filtration conditions for the concentration/diafiltration of other retroviral and lentiviral vectors pseudotyped with different envelope proteins:

In the scientific literature, various envelope proteins were evaluated with a view to studying and improving tropism of the retroviral and lentiviral vectors. In this context, the conditions established for concentration/diafiltration of the GaLV-TR lentiviral vectors were evaluated for the concentration/diafiltration of retroviral and lentiviral vectors pseudotyped with various envelope proteins (Table 4). The results obtained with the GaLV-TR pseudotyped lentiviral vectors are indicated as a reference.

TABLE 4

Concentration/diafiltration of retroviral vectors pseudotyped with various envelope proteins:

| Tangential filtration condition | Retroviral vector | Yield % (TU) |
|---|---|---|
| Bis-Tris, 5% sucrose, 2 mM $MgCl_2$, pH 6.0 | MLV-GaLV (PG13) | 94.2 |
| PBS, 5% sucrose, 2 mM $MgCl_2$, pH 7.0 | LV-GaLV-TR | 73.64 |
| Bis-Tris, 5% sucrose, 2 mM $MgCl_2$, pH 6.0 | LV-GaLV-TR | 63.99 |
| Bis-Tris 5% sucrose 2 mM MgCl2 pH 6.0 | LV-MV-CMHII | 61.22 |
| PBS, 5% sucrose, 2 mM $MgCl_2$, pH 7.0 | LV-MV-CMHII | 65.67 |
| PBS 5% sucrose, 2 mM $MgCl_2$, pH 7.0 | LV-VSV-g | 107 |
| Bis-Tris, 5% sucrose, 2 mM $MgCl_2$, pH 6.0 | LV-VSV-g | 104 |

Note:
MLV-GaLV: GaLV pseudotyped murine retrovirus; LV-GaLV-TR: GaLV-TR pseudotyped lentivirus; LV-MV: pseudotyped lentivirus with the env of the measles virus (CMHII modified); LV-VSV-g: VSV-g pseudotyped lentivirus.

The results presented in Table 4 show that all the retroviral or lentiviral vectors pseudotyped with different envelope proteins may be concentrated in the presence of sucrose and $MgCl_2$ at a pH of 7.0 leading to yields ranging from about 74% for LV-GaLV-TR to about 100% for VSVg. As regards the use of a pH of 6.0 no difference was observed for VSVg pseudotyped vectors.

As regards the GaLV-TR pseudotyped lentiviral vectors, these vectors proved to be more stable at pH 7.0 during tangential filtration. The concentration/diafiltration yield was greater than 90%, while the yield was around 74% for GaLV-TR lentiviral vectors.

Anion Exchange Chromatography:

The concentration/diafiltration step by tangential flow filtration considerably reduced the load of proteins and DNA (see above) meaning that a significant portion of contaminants which may be competitors of the vectors to be purified for accessing the ligands of the chromatography is reduced. In principle, according to the subsequent use, it is possible to imagine two different ways for contemplating purification. They are shown in FIG. 1: a simplified process applying a single exclusion chromatography step (A in FIG. 1) and a more elaborate process applying an additional anion exchange chromatography step with a view to preparing lentiviral vectors for clinical use (B in FIG. 1).

The different chromatography possibilities are developed subsequently:

After the TFF UF/DF step and in order to reduce the contaminants and well separate the viral particles, an anion exchange chromatography step is added. This technique allows separation of the biomolecules according to their isoelectric points depending on the pH and on the salt concentration. Therefore, at a given pH value, a certain salt concentration (often NaCl) is required in order to detach the retained biomolecules and this concentration has to be selected according to the interaction force between the biomolecules and the ligands: the greater this interaction, the higher has to be the salt concentration (salinity). Further, the closer the pH of the chromatography buffer is to the isoelectric point of the species of biomolecules to be purified, the less salt is required for detaching the biomolecules from the chromatographic ligands. However, it is known that retroviral and lentiviral vectors rapidly lose their infectiosity depending on the salt concentration (review by Segura et al. 2006). Therefore, in a first phase, the stability of the lentiviral vectors towards different NaCl concentrations was evaluated.

1. Impact of Salinity on the Stability of the GaLV-TR Lentiviral Vectors:

As indicated above, the elution of the biomolecules retained by a chromatography column is often accomplished with salt gradients (buffers containing NaCl) or a step for increasing the salt concentration (NaCl). Therefore, with a view to evaluating the effect of the NaCl concentration, incubation tests of post-TFF lentiviral vectors were conducted in different NaCl concentrations ranging from 50 mM to 1,500 mM, at room temperature for 4 h. FIG. 3 illustrates the infectivity of the lentiviral vectors at room temperature according to the NaCl concentration as compared with conditions without any added NaCl or the same preparation of vectors incubated at 4° C. without addition of NaCl. This test clearly shows that an NaCl concentration comprised between 50 mM and 1M has a moderately detrimental effect on the stability of the GaLV-TR lentiviral vectors with a loss of infectivity ranging from 29.52% (50 mM NaCl) to 43.86% (1M NaCl) (percentage relative to the preparation stored at 4° C.). On the other hand, the concentration of 1.5M of NaCl leads to a loss of 63.8% of infectivity when the preparation of vectors is stored at room temperature for 4 h. It should be noted that the storage at 20° C. (room temperature) for 4 h without addition of NaCl also leads to a certain loss of infectivity of the vectors by about 23% as compared with storage at 4° C.

These results mean that it is indispensable to elute the GaLV-TR lentiviral vectors of the chromatographic substrates with the lowest possible salinity, therefore ideally below 1M of NaCl with a view to maintaining maximum infectivity. Further, it is also preferable to carry out the totality of the purification (all the steps) at a reduced temperature (ideally between 4° C. and 10° C.).

2. Evaluation of Different Anion Exchange Chromatography Substrates (AEX):

We used low anion exchange chromatography substrates (DEAE (D)) in order to determine whether it was possible to limit the inactivation of the vectors with this type of substrate, in particular by attempting to reduce the required salt concentration for detaching said vectors from the chromatography column. In preliminary tests using a concentrated supernatant from cultures of PG13 cells (MLV-GaLV), it was possible to show that the use of a chromatographic substrate based on DEAE (Tosoh TSK gel DEAE 5PW) leads to an infectious vector yield of about 71% higher than during the use of a strong exchanger (Q Sepharose FF from GE Healthcare) for which the yield was only 16%, due to the too strong interaction leading to inactivation during elution. In this example, the required salt concentration for detaching the retroviral vectors was 655 mM and 915 mM, respectively.

Based on these results, low anion exchangers were selected for the continuation of the development: several chromatography substrates were evaluated: Monolithe CIM D (DEAE), Poros D50 (Life Technologies), Sartobind D (Sartorius) (Bandeira et al. 2012) and Toyopearl 650C DEAE (Merten et al. 2011).

As preliminary tests, three substrates were evaluated aiming to purification of GaLV-TR lentiviral vectors at a pH of 5.5 or 6.0 and 7.0. For all the substrates tested at a pH of 5.5 or 6.0 and 7.0, the low pH choice (5.5 or 6.0) was beneficial as regards infectious vector yield: as regards the CIM D DEAE substrate, the yield was increased from 23% (pH 7.0) to 64% (pH 6.0) during reduction of the pH of the buffers used for the chromatography from 7.0 to 6.0 (FIG. 4). Similar results were observed for the substrates Sartobind 75D (increase in the yield from 5.8% to 15.6%) and Poros D (increase in the yield from 32% (pH 7.0) to 80.2% (pH 6.0) and about 100% (pH 5.5)), and for the gel Toyopearl 650C (increase in the yield from 23% (pH 7.0) to 89% (pH 5.5)) (FIG. 4). Further, in order to detach the vectors from the substrates, the salinity of the elution buffer was able to be lower during chromatography at pH 6.0 (therefore, milder for the lentiviral vectors). As regards the substrate Poros D used at pH 6.0, the elution of the vectors is accomplished at 650 mM of NaCl (see below). In terms of general efficiency, the 'modern' substrates (developed more recently, generating reduced shearing forces (essentially due to the larger porosity than the other substrates) during chromatography and characterized by the incompressibility of the substrate during the modification of the buffer flow rate, like the monolith CIM D DEAE or Poros D) have exhibited yields greater than the yields of substrates with the membrane (Sartobind 75D) or substrates based on a compressible gel (Toyopearl 650C).

Finally, the selection was made on the recent substrates since their efficiency for separating and recovering vectors was greater as compared with more conventional substrates. Both of these supports were therefore more widely evaluated and their use was optimized with a view to purifying lentiviral vectors. Both supports, CIM D DEAE and Poros D, have an interesting yield of more than 60%. The elution occurs at 650 mM NaCl, Bis-Tris 5%, sucrose 2 mM and $MgCl_2$ pH 6.0. An increase in the pH of the elution buffer to 7.0 (PBS) causes a drop in the yield to a value below 7%, but the addition of sucrose 5% to PBS causes a significant increase from about 7% to 40%. However in this case it is necessary to use an NaCl concentration of more than 1M. Indeed, it was observed that for pH 7.0 for eluting the vectors (buffer without additional sucrose) about 1.5 M of NaCl is necessary in PBS, which is probably the explanation of the low yield. The negative effect of the concentration of salts on the stability of the viral particles is known (Segura et al. 2005).

3. Evaluation of Different pH Values on the Chromatography Efficiency by Using the Substrate Poros D:

The pH varied in a range from 5.5 to 8.0 in the presence and in the absence of 5% sucrose. The presence of 5% sucrose has a positive effect on the yield during the anion exchange chromatography step when the pH is greater than 5.5 (for example, Poros D) (Table 5). The positive effect of the presence of sucrose on the yield is no longer observed at pH 5.5. On the other hand, the presence of sucrose is indispensable at a pH of 8.0 with a view to recovering about 58% of infectious vectors. Whereas during the use of a pH ranging from 6.0 to 7.0, the yield is between 52 and 65%, the best yield (about 100%) is obtained at a pH of 5.5.

Generally, the presence of 5% sucrose leads to a reduction in the salinity required for initiating elution of the lentiviral vector with a required decrease of the NaCl concentration by about 25 mM.

TABLE 5

Comparison of the yields of LV-GaLV-TR by chromatography on Poros D by using buffers of various pH (5.5-8.0) in the presence or in the absence of sucrose.

|  | With/without sucrose | Yield in TU % |
| --- | --- | --- |
| pH 5.5 | 5% sucrose | 105.98 |
| (Bis-Tris) | 0% sucrose | 101.33 |
| pH 6.0 | 5% sucrose | 52.32 |
| (Bis-Tris) | 0% sucrose | 29.29 |
| pH 7.0 | 5% sucrose | 65.52 |
| (PBS) | 0% sucrose | 10 |
| pH 8.0 | 5% sucrose | 57.76 |
| (Bis-Tris-propane) | 0% sucrose | 0 |

4. Evaluation of an Alternative Procedure Comprising Anion Exchange Chromatography as a First Step:

We evaluated the yield obtained upon applying an anion exchange chromatography step immediately after the clarification step. Under these conditions, the observed yield is lower than when an ultrafiltration/diafiltration step is applied between the clarification and the anion exchange chromatography. The latter procedure was therefore selected for the subsequent purification.

Exclusion Chromatography:

Exclusion chromatography is a method of choice for separating biomolecules according to their molecular size thus allowing separation of the particles from the contaminants.

The filtration gel Capto Core 700 (GE Healthcare) was used, but other substrates may be contemplated. This step allows us to replace the buffer of the preceding step with the desired formulation buffer, to remove the contaminant molecules of a size of less than 750 kDa and to avoid dilution of the sample to be loaded. This chromatography step may be directly used after tangential flow filtration (concentration/diafiltration—process A) or after an ion exchange chromatography step (process B) (FIG. 1). The sample from the tangential flow filtration or the sample from fractions of the anion exchange chromatography containing the lentiviral vectors is loaded on the exclusion chromatography column. In both cases, the yield of this step is 86%±4, according to the fractions retained for subsequent use.

FIG. 5 shows the purification of lentiviral vectors (concentrated and diafiltered by tangential flow filtration) by filtration on a gel (Capto Core 700). The elution peak of the vector is found at the passage front of the buffer and exit the column at fractions 4-9, covering about 70% of the amount of vectors initially loaded on the column (FIG. 5a). FIGS. 5B and 5C represent the analysis of each fraction by electrophoresis (Western blot, SDS-PAGE) clearly indicating the absence of contaminating bands (FIG. 5C) and the presence of the band at 24-25 kDa corresponding to the protein p24 of the capsid of the lentiviral vector.

Yields and Purities:

The most important parameters relate to the overall yield as well as to the purity of the preparation of lentiviral vectors at the load reduction in contaminating proteins and in contaminating DNA.

As regards the procedure B (including a TFF, an anion exchange chromatography (AEX) and an exclusion chromatography (SEC)) (FIG. 1) intended for purifying lentiviral vectors for clinical use, the yield is of about 50% and this procedure allows 99.9% removal of contaminating proteins and 99.9% of contaminating DNA.

The procedure A (including a TFF and an exclusion chromatography (SEC)) (FIG. 1) intended for the purification of lentiviral vectors for use in research is simpler, since it is without the ion exchange chromatography step. The overall yield is higher because of the reduction in the number of purification steps and attains 60.2%. The removal of the residual DNA contaminants of this simplified procedure is on the order of 96.17% and a reduction of the contaminating proteins of 99.63% is observed.

Practical Examples of Transduction of Target Cells:
Transduction of CD34+ Cells:

In order to determine the quality of the purified vectors, CD34+ umbilical cord blood cells are transduced. The cells are thawed after 18 hours of pre-stimulation with cytokines. The transduction is accomplished for 6 hours. Next, the cells are put in a differentiation medium for 5 days. The cells are then passed to FACS FC500 (BD Biosciences) for measuring the percentage of expression of GFP. The following results are typically obtained (FIG. 6): the purification by concentration/diafiltration of the lentiviral vectors (GaLV-TR) leads to an increase in the transduction efficiency of the CD34+ cells (expressed as a percentage of cells expressing the GFP) ranging from 9% upon the use of a crude supernatant at 70% for use of a preparation of concentrated/diafiltered LV vectors.

Purification of a Pseudotyped Lentiviral Vector by Means of a Modified Envelope of the Measles Virus A process for purifying a lentiviral vector pseudotyped by means of the modified glycoprotein of an envelope of the measles virus (MV pseudotyping) is described here. The LV-MV-CMHII (CMHII=anti-CMHII) lentiviral vectors produced according to the procedure indicated above are purified according to the following steps:

1) Concentration/Diafiltration by Means of a TFF Step
    membrane used: GE #UFP-750-E-3MA 110 cm$^2$, for purification of one liter of product
    diafiltration buffer: PBS (pH 7.0, 2 mM MgCl$_2$, 5% sucrose)
    volume reduction: from 500 mL/1,000 mL to 20 mL, the buffer being replaced with the diafiltration buffer
    yield of infectious vectors: 64-70%
2) Exclusion Chromatography (Gel Filtration):
    column used: Capto Core 700 4.7 mL
    formulation buffer: PBS, 5% sucrose, 2 mm MgCl$_2$, or else X-vivo or HANKS, containing 5% sucrose and 2 mM MgCl$_2$
    equilibration of the column with 10 CV of a formulation buffer
    loading the concentrate from the TFF on the Capto Core 700 column at a rate of 0.5 mL/min washing the column with 20 CV of the formulation buffer
harvesting the samples corresponding to the OD peak
(volume of 21 mL at 50×)
yield of infectious vectors: >90% in TU The overall yield of this purification is from 60 to 63% of infectious vectors, which represents major progress for purification, and therefore the utilization of lentiviral vectors pseudotyped by means of the modified MV glycoprotein.

REFERENCES

Anliker B, Abel T, Kneissl S, Hlavaty J, Caputi A, Brynza J, Schneider I C, Münch R C, Petznek H, Kontermann R E, Koehl U, Johnston I C, Keinänen K, Müller U C, Hohenadl C, Monyer H, Cichutek K, Buchholz C J (2010) Specific gene transfer to neurons, endothelial cells and hematopoietic progenitors with lentiviral vectors. Nat. Methods 7: 929-935.

Ansorge S, Henry O, Kamen A (2010) Recent progress in lentiviral vector mass production. Biochem. Eng. J. 48: 362-377.

Bandeira V, Peixoto C, Rodrigues A F, Cruz P E, Alves P M, Coroadinha A S, Carrondo M J T (2012) Downstream processing of lentiviral vectors: releasing bottlenecks. Hum. Gene Ther. Methods. 23: 255-263.

Charrier S, Ferrand M, Zerbato M, Précigout G, Viornery A, Bucher-Laurent S, Benkhelifa-Ziyyat S, Merten O-W, Perea J, Galy A (2011) Quantification of lentiviral vector copy numbers in individual hematopoietic colony-forming cells shows vector dose-dependent effects on the frequency and level of transduction. Gene Ther. 18: 479-487.

Christodoulopoulos I, Cannon, P M (2001) Sequences in the cytoplasmic tail of the gibbon ape leukemia virus envelope protein that prevent its incorporation into lentivirus vectors. J. Virol. 75: 4129-4138.

Greene M R, Lockey T, Mehta P K, Kim Y S, Eldridge P W, Gray J T, Sorrentino B P (2011) Transduction of human CD34+ repopulating cells with a self-inactivating lentiviral vector for SCID-X1 produced at clinical scale by a stable cell line. Hum. Gene Ther. Methods 23: 297-308.

Fenard D, Ingrao D, Seye A, Buisset J, Genries S, Martin S, Kichler A, Galy A (2013) Vectofusin-1, a new viral entry enhancer, strongly promotes lentiviral transduction of human hematopoietic stem cells. Mol. Ther. Nucleic Acids 2: e90.

Frecha C, Szecsi J, Cosset F L, Verhoeyen E (2008) Strategies for targeting lentiviral vectors. Curr. Gene Ther. 8: 449-460.

Hasslacher M, Mayer C, Mitterer A (2009) Method of concentrating shear-sensitive biopolymers using hollow fibre membranes. WO 2010/025278A1.

Kutner R H, Puthli S, Marino M P, Reiser J (2009) Simplified production and concentration of HIV-1-based lentiviral vectors using HYPERFlask vessels and anion exchange membrane chromatography. BMC Biotechnol. 9: 10.

Merten, O-W (2004) State of art of the production of retroviral vectors. J. Gene Med. 6: S105-S124.

Merten O-W, Charrier S, Laroudie N, Fauchille S, Dugue C, Jenny C, Audit M, Zanta-Boussif M A, Chautard H, Radrizzani M, Vallanti G, Naldini L, Noguiez-Hellin P, Galy A (2011) Large-scale manufacture and characterization of a lentiviral vector produced for clinical ex vivo gene therapy application. Hum. Gene Ther. 22: 343-356.

Miller A D (2001) Production of retroviral vectors. Curr. Protoc. Hum. Genet. Chapter 12: Unit 12.5.

Miller A D, Chen F. (1996) Retrovirus packaging cells based on 10A1 murine leukemia virus for production of vectors that use multiple receptors for cell entry. J. Virol. 70: 5564-5571.

Miller, A D, Garcia, J V, Von, S N, Lynch, C H, Wilson, C, Eiden, M V (1991) Construction and properties of retrovirus packaging cells based on the gibbon ape leukemia virus. J. Virol. 65: 2220-2224.

Münch R C, Mühlebach M D, Schaser T, Kneissl S, Jost C, Plückthun A, Cichutek K, Buchholz C J (2011) DARPins: an efficient targeting domain for lentiviral vectors. Mol. Ther. 19: 686-693.

Pfeifer A, Hofmann A (2009) Lentiviral transgenesis. Methods Mol. Biol. 530: 391-405.

Rodrigues A F, Alves, P M, Coroadinha A S (2011). Production of Retroviral and Lentiviral Gene Therapy Vectors: Challenges in the Manufacturing of Lipid Enveloped Virus. Viral Gene Therapy. K. Xu, InTech. Chapter 2: 15-40.

Sakuma T, De Ravin S S, Tonne J M, Thatava T, Ohmine S, Takeuchi Y, Malech H L, Ikeda Y (2010) Characterization of retroviral and lentiviral vectors pseudotyped with xenotropic murine leukemia virus-related virus envelope glycoprotein, Hum. Gene Ther. 21: 1665-1673.

Schweizer M, Merten O-W (2010) Large-scale production means for the manufacturing of lentiviral vectors. Curr. Gene Ther. 10: 474-486

Segura M M, Kamen A, Garnier A (2006) Downstream processing of oncoretroviral and lentiviral gene therapy vectors. Biotechnol. Adv. 24: 321-337.

Segura M M, Kamen A, Trudel P, Garnier A (2005) A novel purification strategy for retrovirus gene therapy vectors using heparin affinity chromatography. Biotechnol. Bioeng. 90: 391-404.

Stacey G N, Merten O-W (2011) Chapter 3: Host cells and cell banking. In: Merten O-W, Al-Rubeai M (eds.): Viral Vectors for Gene Therapy: Methods and Protocols, in the series of: Methods in Molecular Biology 737, Humana Press, New York, N.Y., pp 45-88.

The invention claimed is:

1. A process for purifying a pseudotyped lentivirus comprising an anion exchange chromatography step, the buffers used during said chromatography being:
   of a pH below 6, or
   of a pH greater than or equal to 6 and further comprising a polyol.

2. The process according to claim 1, said anion exchange chromatography buffer(s) having a pH of less than 6 and also comprising a polyol.

3. The process according to claim 1, the pH of the buffers being between 5.5 and 6.

4. The process according to claim 1, the anion exchange chromatography step being preceded with an ultrafiltration/diafiltration step.

5. The process according to claim 4, the ultrafiltration/diafiltration step comprising the use of one or several buffers with a pH between 5.5 and 7.5, said buffer(s) optionally comprising a polyol.

6. The process according to claim 1, the process comprising:
   (a) clarification of a cell culture medium containing cells producing said pseudotyped lentivirus thereby obtaining a clarified lentivirus;
   (b) an ultrafiltration/diafiltration step for the clarified lentiviruses;
   (c) an anion exchange chromatography; and
   (d) an exclusion chromatography.

7. The process according to claim 6, step (a) being carried out by filtration of the culture medium on a retention filter for which the retention threshold is between 0.2 and 0.45 μm.

8. The process according to claim 6, step (b) being carried out by means of a tangential flow filtration.

9. The process according to claim 6, step (d) comprising the use of an exclusion resin having an exclusion size between 300 and 1,000 kDa.

10. The process according to claim 6, the resin used for the exclusion chromatography being a multimode resin, having a dual functionality of exclusion and adsorption.

11. The process according to claim 1, the purified lentivirus being produced in a neutral medium or in a moderately acid medium.

12. The process according to claim 1, the polyol being selected from sucrose, mannitol, sorbitol and trehalose.

13. The process according to claim 5, the polyol being present in the buffer at a concentration between 1.5% and 15% by weight in the buffer.

14. The process according to claim 4, the polyol being present in the buffers used during the ultrafiltration/diafiltration step and an anion exchange chromatography.

15. The process according to claim 6, the polyol being present in the buffers in all the steps of the purification process.

16. The process according to claim 1, the buffers used during said process also comprising a magnesium salt at a concentration between 0.1 mM and 5 mM.

17. The process according to claim 1, wherein the anion exchange chromatography is a weak anion exchange chromatography and/or an anion exchange chromatography on a column.

18. A process for purifying a pseudotyped lentivirus, said process comprising an ultrafiltration/diafiltration step, said step being carried out using buffers containing a polyol.

19. The process according to claim 1, wherein the lentivirus is pseudotyped with the GaLV-TR, VSV-g or MV envelope glycoprotein.

20. The process according to claim 1, wherein the lentivirus is pseudotyped with the GaLV-TR envelope glycoprotein.

21. The process according to claim 1, wherein the lentivirus is pseudotyped with the VSV-g envelope glycoprotein.

22. The process according to claim 13, wherein the polyol in the buffer is sucrose at a concentration between 2% and 8% by weight.

23. The process according to claim 22, where the polyol in the buffer is sucrose at a concentration of 5% by weight.

* * * * *

UNITED STATES PATENT AND TRADEMARK OFFICE
CERTIFICATE OF CORRECTION

PATENT NO. : 10,465,169 B2  
APPLICATION NO. : 15/105880  
DATED : November 5, 2019  
INVENTOR(S) : Driss Boudeffa, Otto-Wilhelm Merten and David Fenard Page 1 of 1

It is certified that error appears in the above-identified patent and that said Letters Patent is hereby corrected as shown below:

In the Specification

Column 3,
Line 67, "gagpol," should read --*gagpol*,--.

Column 4,
Line 1, "gene rev," should read --gene *rev*,--.
Line 22, "gagpol" should read --*gagpol*--.
Line 24, "lentiviral rev" should read --lentiviral *rev*--.

Column 5,
Line 43, "gagpol" should read --*gagpol*--.
Line 44, "lentiviral rev" should read --lentiviral *rev*--.

Signed and Sealed this
Sixteenth Day of June, 2020

Andrei Iancu
*Director of the United States Patent and Trademark Office*